(12) United States Patent
Bogdanovic et al.

(10) Patent No.: US 11,774,384 B2
(45) Date of Patent: Oct. 3, 2023

(54) SPIN DEFECT MAGNETOMETRY PIXEL ARRAY

(71) Applicant: X Development LLC, Mountain View, CA (US)

(72) Inventors: Stefan Bogdanovic, Mountain View, CA (US); Christian Thieu Nguyen, San Diego, CA (US)

(73) Assignee: X Development LLC, Mountain View, CA (US)

( * ) Notice: Subject to any disclaimer, the term of this patent is extended or adjusted under 35 U.S.C. 154(b) by 248 days.

(21) Appl. No.: 17/149,848

(22) Filed: Jan. 15, 2021

(65) Prior Publication Data

US 2022/0228998 A1    Jul. 21, 2022

(51) Int. Cl.
*G01N 24/10* (2006.01)
*G01R 33/32* (2006.01)
*G01R 33/032* (2006.01)

(52) U.S. Cl.
CPC ........... *G01N 24/10* (2013.01); *G01R 33/032* (2013.01); *G01R 33/32* (2013.01)

(58) Field of Classification Search
None
See application file for complete search history.

(56) References Cited

U.S. PATENT DOCUMENTS

| | | | |
|---|---|---|---|
| 8,547,090 | B2 | 10/2013 | Lukin et al. |
| 8,947,080 | B2 | 2/2015 | Lukin et al. |
| 9,245,551 | B2 | 1/2016 | Hallak et al. |
| 9,541,610 | B2 | 1/2017 | Kaup et al. |
| 9,557,391 | B2 | 1/2017 | Egan et al. |
| 9,823,313 | B2 | 11/2017 | Hahn et al. |
| 9,823,314 | B2 | 11/2017 | Hahn et al. |
| 9,851,418 | B2 | 12/2017 | Wolf et al. |
| 9,910,105 | B2 | 3/2018 | Boesch et al. |
| 10,006,973 | B2 | 6/2018 | Hahn et al. |
| 10,012,704 | B2 | 7/2018 | Coar |

(Continued)

FOREIGN PATENT DOCUMENTS

| | | |
|---|---|---|
| CN | 208125759 | 11/2018 |
| CN | 208255383 | 12/2018 |

(Continued)

OTHER PUBLICATIONS

Patel et al., "Sub-nanotesla magnetometry with a bre-coupled diamond sensor," CoRR, Feb. 2020, arxiv.org/abs/2002.08255, 14 pages.

*Primary Examiner* — Jay Patidar
(74) *Attorney, Agent, or Firm* — Fish & Richardson P.C.

(57) ABSTRACT

A magnetometry apparatus includes an array of magnetometer pixels. Each magnetometer pixel includes an electron spin defect body including a plurality of lattice point defects, and a microwave field transmitter operable to apply a microwave field to the electron spin defect body. The apparatus may also include an optical source configured to emit input light of a first wavelength that excites the plurality of lattice point defects of the electron spin defect bodies from a ground state to an excited state, and a photodetector arranged to receive photoluminescence of a second wavelength emitted from a first electron spin defect body of a first magnetometer pixel of the array of magnetometer pixels. The second wavelength is different from the first wavelength.

32 Claims, 12 Drawing Sheets

(56) References Cited

U.S. PATENT DOCUMENTS

| | | |
|---|---|---|
| 10,082,545 B2 | 9/2018 | Jeske et al. |
| 10,123,714 B2 | 11/2018 | Hatano et al. |
| 10,126,377 B2 | 11/2018 | Hahn et al. |
| 10,168,393 B2 | 1/2019 | Stetson et al. |
| 10,274,551 B2 | 4/2019 | Hruby et al. |
| 10,330,744 B2 | 6/2019 | Luzod |
| 10,338,164 B2 | 7/2019 | Hahn et al. |
| 10,345,396 B2 | 7/2019 | Manickam et al. |
| 10,359,479 B2 | 7/2019 | Manickam et al. |
| 10,379,069 B2 | 8/2019 | Hatano et al. |
| 10,408,890 B2 | 9/2019 | Bruce et al. |
| 10,459,041 B2 | 10/2019 | Hahn et al. |
| 10,495,698 B2 | 12/2019 | Jeske et al. |
| 10,502,796 B2 | 12/2019 | Hatano et al. |
| 10,564,231 B1 | 2/2020 | Mandeville et al. |
| 10,677,953 B2 | 6/2020 | Stetson et al. |
| 10,712,408 B2 | 7/2020 | Pham et al. |
| 10,753,990 B2 | 8/2020 | Niu et al. |
| 10,816,616 B2 | 10/2020 | Manickam et al. |
| 2017/0023487 A1* | 1/2017 | Boesch ............... G01R 33/032 |
| 2017/0234941 A1* | 8/2017 | Hatano ............... G01R 33/032 324/304 |
| 2017/0343695 A1* | 11/2017 | Stetson ............... G01R 33/032 |
| 2019/0018076 A1 | 1/2019 | Hahn et al. |
| 2019/0018088 A1 | 1/2019 | Hu et al. |
| 2019/0219645 A1 | 7/2019 | Hahn et al. |
| 2019/0235031 A1 | 8/2019 | Ibrahim et al. |
| 2020/0049776 A1 | 2/2020 | Wood et al. |
| 2020/0158798 A1 | 5/2020 | Huck et al. |
| 2020/0281499 A1 | 9/2020 | Maeda et al. |
| 2020/0305747 A1 | 10/2020 | Kudo et al. |
| 2020/0347515 A1 | 11/2020 | Markham et al. |
| 2020/0348378 A1 | 11/2020 | Alford et al. |
| 2021/0255254 A1* | 8/2021 | Lo ....................... G01R 33/02 |

FOREIGN PATENT DOCUMENTS

| | | | |
|---|---|---|---|
| CN | 106414818 | 4/2019 | |
| CN | 110133545 | 8/2019 | |
| CN | 110325869 | 10/2019 | |
| CN | 105223521 | 2/2020 | |
| CN | 210347904 | 4/2020 | |
| CN | 108732518 B * | 5/2020 | ......... G01R 33/0052 |
| CN | 111175678 | 5/2020 | |
| CN | 111198344 | 5/2020 | |
| CN | 108983121 | 7/2020 | |
| CN | 111426992 | 7/2020 | |
| CN | 111568418 | 8/2020 | |
| CN | 110554332 | 1/2021 | |
| DE | 102018202588 | 8/2019 | |
| DE | 102018208055 | 11/2019 | |
| DE | 102018214617 | 3/2020 | |
| DE | 102018216033 | 3/2020 | |
| DE | 102018220234 | 5/2020 | |
| DE | 102019203929 | 9/2020 | |
| DE | 102019203930 | 9/2020 | |
| EP | 3242139 | 11/2017 | |
| EP | 3373023 | 9/2018 | |
| GB | 2574643 | 12/2019 | |
| WO | WO2019168097 | 9/2019 | |
| WO | WO2020157497 | 8/2020 | |

* cited by examiner

SPIN DEFECT MAGNETOMETRY PIXEL ARRAY

BACKGROUND

Various sensors are available that rely on classical physical phenomena for detecting properties such as electric or magnetic fields. In certain cases, magnetic field detectors are limited by one or more of their sensitivity, dynamic range and/or form factor.

SUMMARY

The present disclosure relates to spin defect magnetometry imaging. In some examples, the disclosure describes a magnetometry apparatus including an array of magnetometer pixels. Each magnetometer pixel includes an electron spin defect body including a plurality of lattice point defects, and a microwave field transmitter operable to apply a microwave field to the electron spin defect body. The apparatus may also include an optical source configured to emit input light of a first wavelength that excites the plurality of lattice point defects of the electron spin defect bodies from a ground state to an excited state, and a photodetector arranged to receive photoluminescence of a second wavelength emitted from a first electron spin defect body of a first magnetometer pixel of the array of magnetometer pixels. The second wavelength is different from the first wavelength.

Examples of magnetometry apparatuses may include any one or more of the following features. Each magnetometer pixel includes a corresponding substrate on which the electron spin defect body of the magnetometer pixel is disposed. The magnetometry apparatus includes a substrate on which the electron spin defect bodies of the array of magnetometer pixels are disposed. The substrate includes a metal trace that electrically couples the photodetector to a processor disposed on the substrate.

Examples of magnetometry apparatus may include any one or more of the following features. The magnetometry apparatus includes a plurality of photodetectors. Each photodetector of the plurality of photodetectors is arranged to detect photoluminescence emitted from a corresponding magnetometer pixel. The photodetector is arranged to receive photoluminescence from a plurality of the electron spin defect bodies. The photodetector includes a light collecting pixel array, and the photodetector and the plurality of electron spin defect bodies are arranged such that respective photoluminescences emitted from the plurality of electron spin defect bodies are received at respective distinct portions of the light collecting pixel array. The magnetometry apparatus includes a plurality of lenses arranged to focus the respective photoluminescences onto the respective distinct portions of the light collecting pixel array.

Examples of magnetometry apparatuses may include any one or more of the following features. The magnetometry apparatus includes a computing device coupled to the photodetector. The computing device is configured to perform operations including receiving, from the photodetector, a signal indicative of photoluminescence emitted from the one or more of the electron spin defect bodies, and reconstructing a spatial map of a second magnetic field to which the array of magnetometer pixels is exposed based, at least in part, on the signal indicative of photoluminescence. Reconstructing the spatial map includes generating an image representing the second magnetic field to which the array of magnetometer pixels is exposed. The operations include normalizing respective magnetic field responses of each of the magnetometer pixels.

Examples of magnetometry apparatuses may include any one or more of the following features. Each magnetometer pixel includes a corresponding parabolic reflector. Each parabolic reflector defines an internal cavity in which the electron spin defect body of the magnetometer pixel is arranged. Each magnetometer pixel includes a corresponding optical filter configured to pass light of the second wavelength and block light of the first wavelength. Each parabolic reflector includes an opening through which the input light of the first wavelength passes.

Examples of magnetometry apparatuses may include any one or more of the following features. The magnetometry apparatus includes a first optical fiber arranged to carry the input light from the optical source to the first electron spin defect body; and a second optical fiber arranged to carry the photoluminescence from the first electron spin defect body to the photodetector. The first optical fiber and the second optical fiber are attached to the electron spin defect body of the first magnetometer pixel. The magnetometry apparatus includes at least one optical filter between the array of magnetometer pixels and the photodetector. The at least one optical filter is configured to pass light of the second wavelength and block light of the first wavelength. The magnetometry apparatus includes a magnet configured to apply a magnetic field to the array of magnetometer pixels. The electron spin defect bodies of the array of magnetometer pixels are disposed on a first substrate, and the microwave field transmitters of the array of magnetometer pixels are disposed on a second substrate. The first substrate is mounted on the second substrate such that each electron spin defect body is aligned with a corresponding microwave field transmitter.

This disclosure also describes methods. In some examples, the disclosure describes a method of spatially mapping a time-varying magnetic field. In some implementations, the method includes directing input light of a first wavelength to each magnetometer pixel of an array of magnetometer pixels, each magnetometer pixel including a corresponding electron spin defect body including a plurality of lattice point defects; exposing the corresponding electron spin defect body of each magnetometer pixel of the array of magnetometer pixels to the time-varying magnetic field; detecting, at a photodetector, photoluminescence of a second wavelength emitted from a first electron spin defect body of a first magnetometer pixel of the array of magnetometer pixels, where the second wavelength is different from the first wavelength; obtaining a signal from the photodetector, wherein the signal is indicative of the photoluminescence; and reconstructing a spatial map of the time-varying magnetic field based, at least in part, on the signal.

In some examples, the method includes any one or more of the following features. Reconstructing the spatial map includes generating an image representing spatially-resolved magnetic field strengths of the time-varying magnetic field. The method includes normalizing respective magnetic field responses of each of the magnetometer pixels. Directing the input light includes providing the input light into each optical fiber of a plurality of optical fibers, each optical fiber of the plurality of optical fibers having an end attached to a corresponding magnetometer pixel of the array of magnetometer pixels. Each optical fiber is arranged to direct the input light into the electron spin defect body of the corresponding magnetometer pixel.

In some examples, the method includes any one or more of the following features. Each magnetometer pixel includes a corresponding parabolic reflector, wherein the parabolic reflector defines an internal cavity in which the electron spin defect body of the magnetometer pixel is arranged, and directing the input light includes directing the input light through respective openings in the parabolic reflectors. The method includes filtering the photoluminescence to block light of the first wavelength and pass light of the second wavelength. The method includes applying microwave signals to the electron spin defect bodies of the array of magnetometer pixels. The method includes applying a second magnetic field to the electron spin defect bodies of the array of magnetometer pixels.

In some implementations, the method includes: detecting, at a plurality of photodetectors, respective photoluminescences emitted from a plurality of electron spin defect bodies of the magnetometer pixels of the array of magnetometer pixels, where each photodetector of the plurality of photodetectors detects photoluminescence from a corresponding magnetometer pixel; obtaining, from the plurality of photodetectors, a plurality of respective signals indicative of the respective photoluminescences; and reconstructing the spatial map based on the plurality of respective signals.

Implementations according to the present disclosure may provide one or more of the following advantages. In some implementations, magnetic fields may be imaged with higher sensitivity, lower noise, or both. In some implementations, a magnetometer is made more compact. In some implementations, signals corresponding to multiple individual magnetometer pixels are differentiated for a combined measurement.

The details of one or more embodiments are set forth in the accompanying drawings and the description below. Other features, objects, and advantages of the invention will be apparent from the description and drawings, and from the claims.

DETAILED DESCRIPTION

The present disclosure relates to electron spin defect-based magnetometry imaging. In particular, the present disclosure relates to the use of multiple electron spin defect bodies to perform spatially-resolved magnetic field sensing. Zeeman shifts of electron spin sublevels established by the presence of atomic defects in the electron spin defect bodies are monitored in order to sense local magnetic fields to which each electron spin defect body is exposed, and the individual magnetic field readings may be combined for spatial magnetic field mapping.

More specifically, electron spin defect based magnetometers include quantum sensors that leverage the occurrence of an electronic spin defect in a solid state lattice, where the spin can be both initialized and read out optically. In certain implementations, the defect may arise as an atomic-level vacancy in a lattice structure (sometimes called a "defect body"), such as a vacancy occurring near a nitrogen atom substituted in place of a carbon atom within diamond. Accordingly, a single spin defect center, as an atom-scale defect, may be used to detect magnetic fields with nanometer spatial resolution, while an ensemble of uncorrelated spin defects may be used with spatial resolution given by the ensemble size (e.g., on the order of microns) typically with an improvement in sensitivity given by N, where N is the number of spin defects. Moreover, in some implementations, electron spin defect based magnetometers may exhibit relatively long coherence times, such as times approaching 1 second or more. Additionally, electron spin defect based magnetometers may be operated at room temperature and, in certain cases, within relatively compact structures, allow for portability and reduction in magnetometer costs, which may be advantageous in health related applications such as measuring magnetic fields emanating from the heart.

Figure 1:
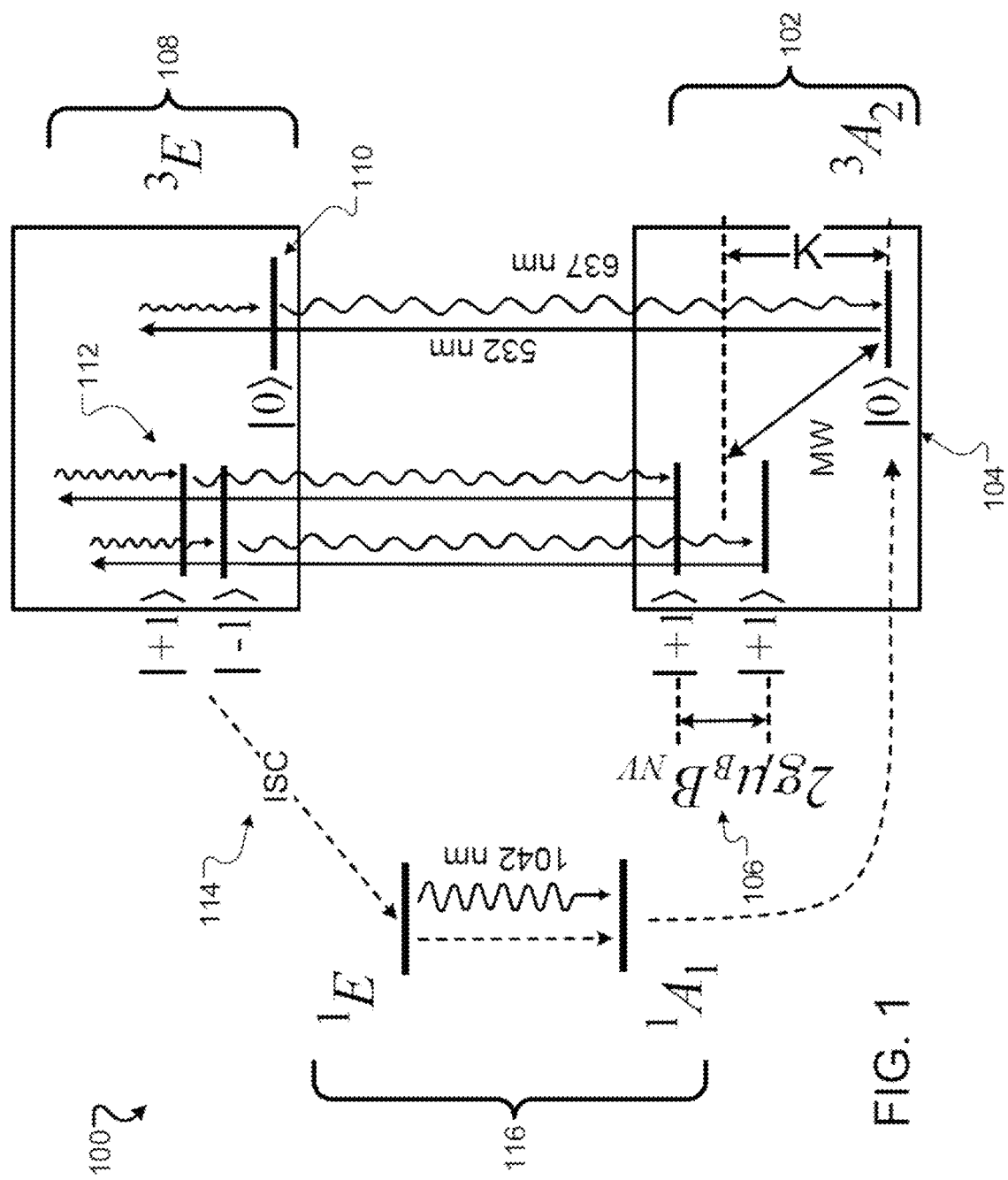
FIG. 1 is a schematic that illustrates an exemplary energy level scheme for a nitrogen-vacancy defect.

A brief description of electron spin defect based magnetometry will be described with reference to FIGS. 1-2 and in particular with respect to nitrogen vacancy (NV) magnetometry, though the techniques and devices disclosed herein may be applicable to other materials, including other types of electron spin defects, as well. An NV center is a defect in a diamond lattice (defect body) that contains a substitutional nitrogen atom in place of carbon, adjacent to a vacancy in the diamond lattice. The negatively-charged state of the defect provides a spin triplet ground level which can be initialized, coherently manipulated with long coherence time and readout, using optical means. FIG. 1 is a schematic that illustrates an energy level scheme 100 for an NV defect. The NV defect behaves as an artificial atom within the diamond lattice that exhibits a broadband photoluminescence emission with a zero phonon line at 1.945 eV or $\lambda_{PL}$=637 nm. Moreover, the ground level 102 of the NV defect is a spin triplet state, having spin sub-levels of the $m_s$=0 state 104 and the $m_s$=+/−1 states 106, separated by K=2.87 GHz in the absence of a magnetic field. The defect can be optically excited to an excited level 108, which also is a spin triplet having an $m_s$=0 state 110 and $m_s$=+/−1 states 112. Once optically excited into the excited level 108, the NV defect can relax primarily through one of two mechanisms: a) through a radiative transition and phonon relaxation, thus producing a broadband red photoluminescence; or b) through a secondary path 114 that involves non-radiative intersystem crossing to singlet states 116.

The decay path branching ratios from the excited state manifold back to the ground state manifold depends on its initial spin sublevel projection. Specifically, if the electron spin began in the $m_s$=+/−1 states, there is approximately a 30% chance for the spin to decay non-radiatively through the secondary path 114, down to the $m_s$=0 state. The population of the spin sublevels can be manipulated by the application of a resonant microwave field to the diamond.

Specifically, at a particular microwave frequency corresponding to the transition energy cost between the 0 and +/−1 states, transitions occur between those sublevels, resulting in a change in the level of photoluminescence of the system. In particular, if the spin is initialized into the $m_s=0$ state, and the population is transferred to one of the +/−1 states by the resonant microwave drive, the photoluminescence rate upon subsequent optical illumination will decrease.

Figure 2:
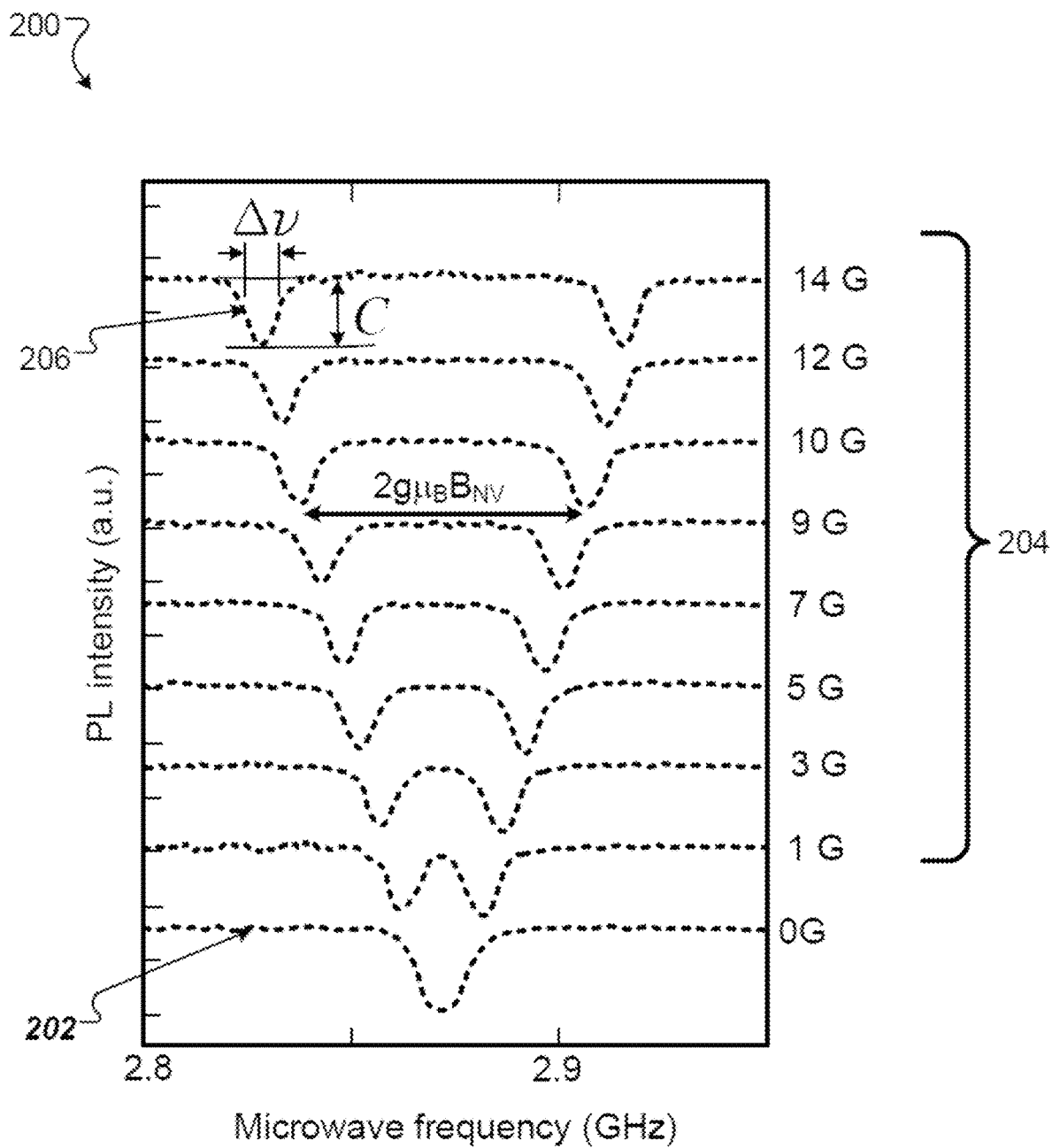
FIG. 2 is a plot of exemplary photoluminescence intensity versus applied microwave frequency.

This drop in photoluminescence may be observed by sweeping the microwave frequency, as depicted in the bottom-most photoluminescence (PL) intensity line 202 shown in FIG. 2, which is a plot of PL intensity versus applied microwave frequency. Upon applying a magnetic field in the vicinity of the NV defect, however, the degeneracy of the $m_s=+/-1$ spin sublevels is lifted by the Zeeman effect, leading to the appearance of two electron spin resonance (ESR) transitions, corresponding to dips in the PL spectrum (see upper PL lines 204 in FIG. 2). The value Δv corresponds to the ESR linewidth, typically on the order of 1 MHz, and the value C is the ESR contrast, typically on the order of a few percent. To detect small magnetic fields, the NV transitions may be driven at the point of maximum slope (see, e.g., 206 in FIG. 2). At this point of maximum slope, a time-domain change in the photoluminescence may be detected, from which a time-domain change in magnetic field can be derived. The signal may be expressed as $(\partial I_0/\partial B) \times \delta B \times \Delta t$, where $I_0$ is the NV defect PL rate, $\delta B$ is the infinitesimal magnetic field variation, and $\Delta t$ is the measurement duration, much smaller than the timescale on which the magnetic field changes A single NV defect therefore can serve as a magnetic field sensor with an atomic-sized detection volume. To improve sensitivity, a collective response of an ensemble of NV defects may be detected, such that the collected PL signal is magnified by the number N of the sensing spins and therefore improves the shot-noise limited magnetic field sensitivity by a factor of $1/\sqrt{N}$.

Figure 3:
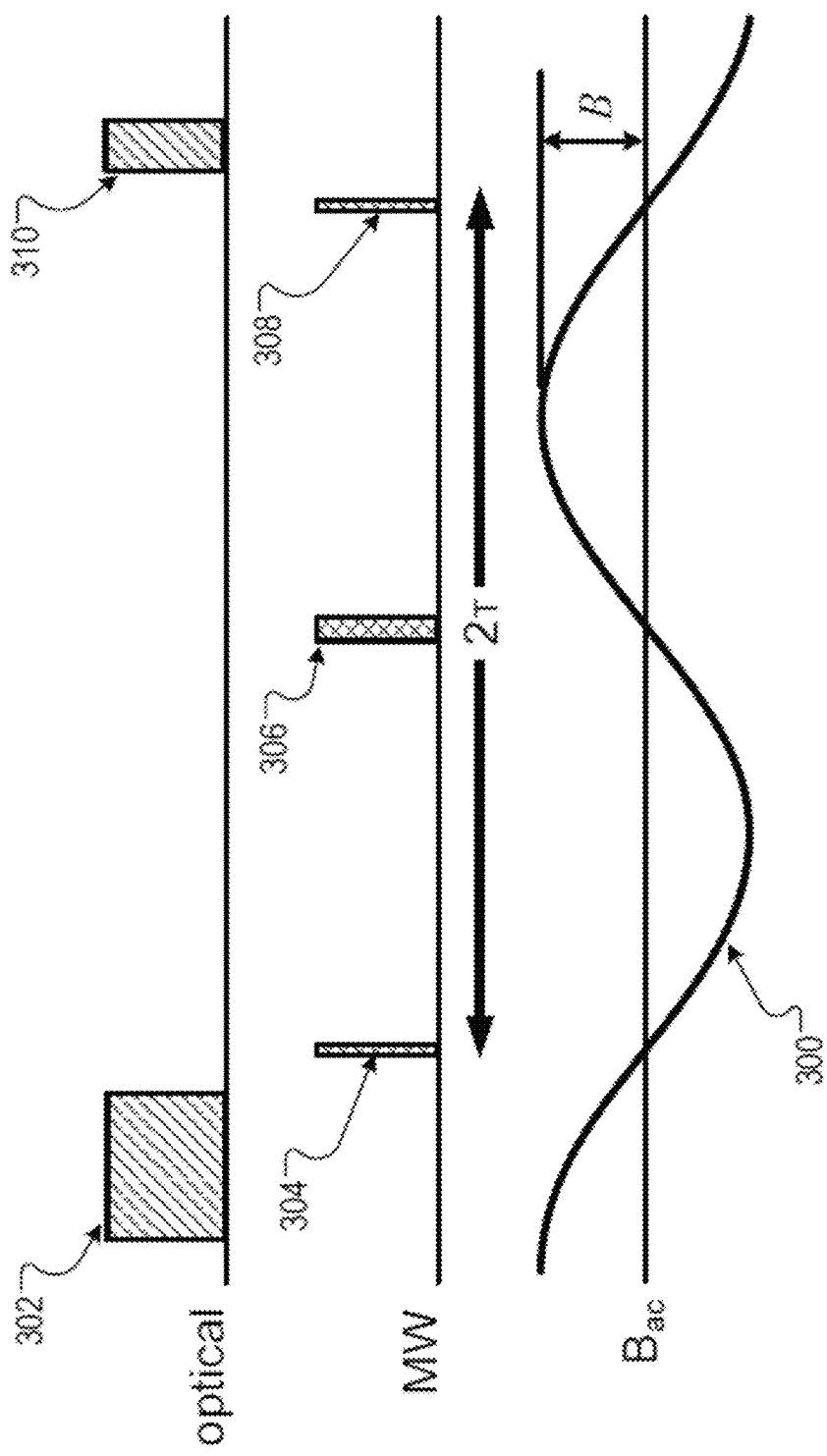
FIG. 3 is a schematic that illustrates an exemplary process for performing electron spin defect based magnetometry to detect an AC magnetic field.

Magnetic field sensitivity can further be improved if the magnetic field to be measured is periodic in time (e.g., an AC field). The improvement in sensitivity with a classical AC field is a result of a prolongation of the NV spin coherence that can be achieved through dynamical decoupling of the central spin from its environment. To avoid broadening of the ESR linewidth caused by the laser readout process and the driving microwave field, the spin manipulation, spin readout and phase accumulation (magnetic field measurement) may be separated in time. To do so, a series of microwave pulses are applied in sequence to the NV defect (or defects) that is in a prepared state |0>. Here |0> and |1> denote the electron spin states $m_s=0$ and $\underline{m}_s=1$. FIG. 3 is a schematic that illustrates an example of electron spin defect based magnetometry for an AC magnetic field, in which a microwave pulse sequence is applied to an NV defect or ensemble of NV defects. The pulse sequence may also referred to as the "Hahn echo," though other dynamical decoupling pulse sequences may be used instead. In particular, a first light pulse 302 is applied to the NV defect, or ensemble of NV defects, to place them in a prepared state |0>. While the NV defect(s) are exposed to an alternating magnetic field 300, a first π/2 microwave pulse 304, is applied to the NV defect(s) to rotate the electron spin of the NV defect(s) from the prepared state |0> to a coherent superposition $|\psi\rangle = 1/\sqrt{2} \ast (|0\rangle + e^{i\varphi}|1\rangle)$ which evolves over a total free precession time 2τ, if the microwave drive Rabi frequency is larger than other terms in the Hamiltonian, such as NV hyperfine coupling and the size of the magnetic field to be measured. The phase φ may be set to zero by definition, choosing the microwave drive field to be along the y axis (arbitrarily). During the free precession time, the electron spin interacts with the external magnetic field. The |1> state acquires a phase with respect to the |0> state, corresponding to a precession of the spin in the plane perpendicular to the spin quantization axis in a Bloch sphere picture. Then, a first π microwave pulse 306 is applied to "swap" the phase acquired by the |0> and |1> states. For slow components of the environmental magnetic noise, the dephasing acquired during the first half of the sequence is compensated and spin dephasing induced by random noise from the environment may be reduced. Additionally, frequency components much higher than the frequency 1/τ average out to zero. Slow components may include, e.g., DC components and low frequency components on the order of several Hz, several tens of Hz, several hundreds of Hz, and 1-1000 kHz such as 10 Hz or less, 100 Hz or less, or 500 Hz or less, 1 kHz or less, 10 kHz or less, 100 kHz or less and 1 MHz or less. In some implementations, the pulse 306 is applied at the zero crossing of the classical AC magnetic field so that the spin phase accumulation due to the classical AC field can be enhanced. In some implementations, multiple π microwave pulses 306 are applied periodically. After applying one or more π microwave pulses 306, the phase φ and thus the magnetic field is measured by applying a second π/2 pulse 308 that projects the NV electronic spin back onto the quantization axis. The total phase accumulation is thus converted into an electron population, which may be read out optically through the spin-dependent PL of the NV defect(s). That is, a second optical pulse 310 is applied to the NV defect, or ensemble of NV defects, resulting in a photoluminescence that is read out by an optical detector. To derive the magnetic field B(t) from the PL measurement, the function describing the evolution of the $S_z$ operator under the pulse sequence is multiplied by the noise and signal fields, which is then integrated to get the phase accumulation and subsequently multiplied by contrast and total photoluminescence rate to get the photoluminescence signal (sine magnetometry). For cosine magnetometry, the filter function is convolved with the power spectral density of the noise and signal fields to get the phase variance, which is then multiplied by contrast and photoluminescence rate. Sensitivity compared to the continuous-wave driving technique may improve by a factor of at least $(T2/T2\ast)^{1/2}$, in which T2 is the coherence time of the NV under AC magnetometry and T2* is inversely proportional to the NV linewidth.

An NV defect is just one example of a type of spin defect that may be used to perform electron spin defect based magnetometry using electron spin defect bodies. In other implementations, one or more spin defects may be formed in silicon carbide. SiC defects include defects due to other substitutional atoms, such as, e.g. phosphorus, in the SiC lattice. Similar techniques for detecting magnetic fields as described herein with NV defects may be employed with the SiC defects.

According to some embodiments of this disclosure, an array of individual magnetometer pixels is used to spatially map a sensed magnetic field according to the physical principles described above.

Figure 4:
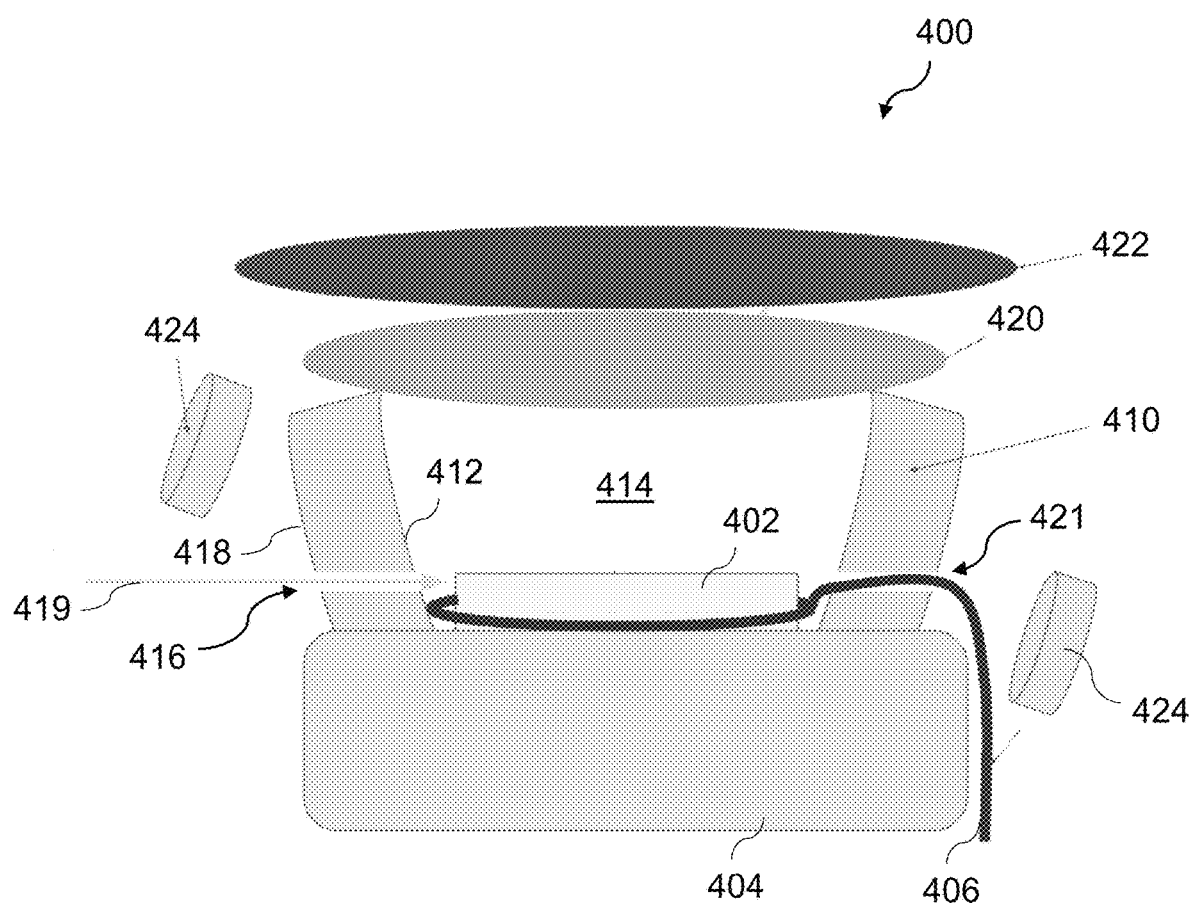
FIG. 4 is a schematic that illustrates an exemplary magnetometer pixel.

FIG. 4 shows a schematic of an example magnetometer pixel 400. The magnetometer pixel 400 includes an electron spin defect body 402 which is disposed on a substrate 404. The electron spin defect body 402 includes multiple lattice point defects, such as NV defects formed in diamond, as described herein. The electron spin defect body 402 containing the NV defects may be formed, in some implementations, from up to 99.999% carbon 12. In some implementations, carbon 13 is used partially in place of carbon 12.

The electron spin defect body 402 is not limited to NV defects formed in diamond, and may include other lattice point defects in other materials, such as substitutional phosphorus atoms in silicon carbide, vacancies in silicon carbide (e.g., silicon vacancies), InGaAs quantum dots, and neutrally-charged silicon vacancies (SiV$^0$) in diamond. The electron spin defect body 402 may be a sub-portion of a larger body that is without electron spin defects. For example, the electron spin defect body 402 may be a top layer or top portion of a diamond body, with the rest of the diamond body (not shown) having no electron spin defects or fewer electron spin defects.

Dimensions of the electron spin defect body 402 can vary. For example, in some implementations, a thickness of the electron spin defect body 402 is less than about 1 millimeter, such as less than 750 microns, less than 500 microns, less than 250 microns, or less than 100 microns. In some implementations, the thickness is greater than about 10 microns, such as greater than 50 microns, greater than 100 microns, greater than 250 microns, greater than 500 microns, or greater than 750 microns. Other thicknesses may be used as well. Thickness of the electron spin defect body 402, as defined here, can refer to a smallest dimension of the electron spin defect body. In some cases, the thickness of the electron spin defect body 402 is defined as a distance from a surface of the electron spin defect body 402 in contact with the substrate 404 to an opposite surface of the electron spin defect body 402. In some cases, the thickness is defined as a distance from a surface of the electron spin defect body 402 delimiting the electron spin defect body 402 with respect to a larger body of which the electron spin defect body 402 is a part (as described above), to an opposite surface of the electron spin defect body 402.

Lateral dimensions of the electron spin defect body 402 (e.g., dimensions orthogonal to the thickness, such as length and width) can also vary. For example, in some implementations a width of the electron spin defect body 402 is greater than about 0.1 mm, such as greater than 0.5 mm, greater than 1 mm, greater than 2 mm, greater than 3 mm, or greater than 5 mm. In some implementations, the width is less than about 5 cm, such as less than 3 cm, less than 1 cm, or less than 5 mm. Other widths may be used as well.

In some implementations, the electron spin defect body 402 (or a larger body of which the electron spin defect body 402 is a part) is secured to the substrate 404 using an adhesive including, e.g., epoxies, elastomers, thermoplastics, emulsions, and/or thermosets, among other types of adhesives.

As described in further detail below, electrical and/or optical connections may be formed from the electron spin defect body 402, or a larger body of which the electron spin defect body 402 is a part, to electrical and/or optical elements formed on in and the substrate 404. The substrate 404 may have more than one electron spin defect body, corresponding to more than one magnetometer pixel, disposed thereon, e.g., as an array of magnetometer pixels.

The magnetometer pixel 400 further includes a microwave field transmitter 406 that is configured to provide a microwave field to the electron spin defects of the electron spin defect body 402. In this example, the microwave field transmitter 406 includes a conductive loop formed around the electron spin defect body 402. In various implementations, the microwave field transmitter 406 may include a thin film antenna formed on a surface of the electron spin defect body 402, such as an outer-facing surface of the electron spin defect body 402, at an interface between the electron spin defect body 402 and a larger body of which the electron spin defect body 402 is a part, and/or on or in the substrate 404. The microwave field transmitter 406 may include a co-planar waveguide, a wire, a loop or a coil of electrically conductive material, such as metal. The microwave field transmitter 406 may be positioned adjacent to an area of the electron spin defect body 402 to which an input optical fiber is attached, as described in more detail below.

As described in further detail below, the microwave field transmitter 406 may be coupled to a microwave field control circuit that drives the microwave transmission.

The magnetometer pixel 400 also includes a reflector 410, which may be mounted on the substrate 404, e.g., by an epoxy or a glue. The reflector 410 may be oriented circumferentially around the electron spin defect body 402, e.g., surround the electron spin defect body except for openings and/or holes defined by the reflector 410. The reflector 410 includes a reflective inner surface 412 that is reflective to photoluminescence emitted by spin defects within the electron spin defect body 402. For example, the reflective inner surface 412 may be at least about 90% reflective to the photoluminescence, at least about 95% reflective to the photoluminescence, or at least about 99% reflective to the photoluminescence.

In some implementations, the inner surface 412 is reflective for wavelengths between about 620 nm and about 800 nm.

The electron spin defect body 402 is arranged inside a cavity 414 defined by the reflector 410, such that at least some photoluminescence emitted from the electron spin defects is reflected off the reflective inner surface 412 of the electron spin defect body.

In some implementations, the reflector 410 is shaped such that the reflector 410 causes collection of the emitted photoluminescence. For example, the inner surface 412 of the reflector 410 may be a rotated, truncated parabola having a focus that coincides with the electrons spin defect body 402. In some implementations, the inner surface 412 of the reflector 410 is a truncated, inverted hollow cone. Other reflector shapes are also within the scope of this disclosure, e.g., parabolas or cones including deformations from a perfect parabolic or conical shape.

In some implementations, a first base of the hollow cone or parabola (e.g., a wider of two bases of the hollow cone or parabola) has a radius of about 10 mm. In some implementations, a second base of the hollow cone or parabola (e.g., a narrower of the two bases, resting on the substrate 404) has a radius of about 1.5 mm or about 2 mm. In some implementations, the first base has a radius between 5 mm and 12 mm. In some implementations, the second base has a radius between 1 mm and 3 mm.

In some implementations, the reflective inner surface 412 is made of polished metal. In some implementations, the reflective inner surface 412 is made of a polished metal-coated plastic or ceramic.

Figure 5:
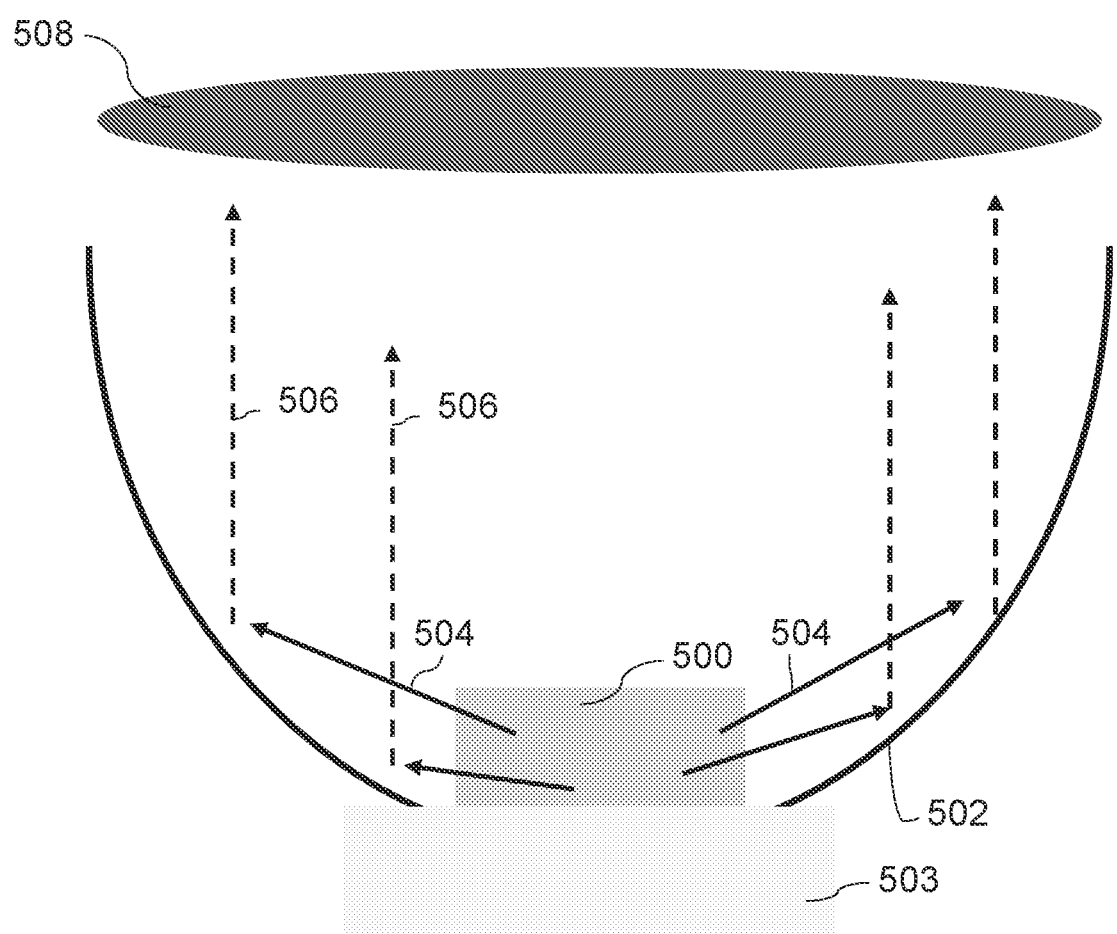
FIG. 5 is a schematic that illustrates an exemplary reflector in a magnetometer pixel.

FIG. 5 is a schematic that shows an example of light reflection from an electron spin defect body 500 in a cavity defined by a parabolic reflector 502. The electron spin defect body and the parabolic reflector are disposed on a substrate 503.

Photoluminescence 504 emitted by the electron spin defect body 500 reflects off inner walls of the parabolic reflector 502. The electron spin defect body 500 is arranged (e.g., is disposed at a focal point of the parabolic reflector 502) such that the emitted photoluminescence 504, regardless of original emission direction, is reflected into substantially collimated parallel optical paths 506, effectively forming a beam/plane wave of photoluminescence. The reflected light traveling on the optical paths 506 can then be collected by a photodetector 508. In some implementations, the parabolic reflector 502 reflects the photoluminescence towards another optical element, e.g., a lens, wavelength filter, polarizer, or beam splitter, among others.

Referring back to FIG. 4, in the absence of the reflector 410, much of the photoluminescence might be lost, e.g., portions of the photoluminescence that are not emitted directly towards a collection lens or photodetector. However, the reflector 410 collects photoluminescence from a wide solid angle of emission, such that significantly more of the photoluminescence may be collected/detected compared to if there were no reflector 410. This can increase a sensitivity and/or reliability of magnetic field sensing, e.g., decrease a level of noise, increase a signal-to-noise ratio of the photoluminescence, or decrease a minimum detectable magnetic field strength by increasing measured photoluminescence.

In some implementations, a quantum efficiency of photoluminescence detection is increased from about 4% to about 90% or higher, compared to a magnetometer without a reflector. In various implementations, the quantum efficiency is between about 10% and 99%, between about 20% and 99%, or between about 50% and 99%. The quantum efficiency is the ratio of detected photons captured by detectors to input photons emitted by the optical source. Higher quantum efficiencies correspond to more sensitive magnetic detection, less detection noise, or both.

In the example shown in FIG. 4, the reflector 410 includes a first hole 416, e.g., a hole from an outer surface 418 of the reflector 410 to the inner surface 412. Input light 419 that excites the spin defects of the electron spin defect body 402 may be directed from outside the cavity 414 through the first hole 416 to illuminate the electron spin defect body 402. Generation of the input light 419 is described in further detail in reference to FIG. 6.

In this example, the reflector 410 also includes a second hole 421 through which the microwave field transmitter 406 passes. In some implementations, the microwave field transmitter 406 is mounted outside the reflector. In some implementations, other holes may also be provided to allow for coupling of other elements from outside the cavity 414 to inside the cavity 414. In some implementations, instead of or in addition to holes, light is transmitted through transparent windows integrated into reflectors. For clarity, holes are not shown in FIG. 5.

The example magnetometer pixel 400 includes an optical filter 420. The optical filter 420 is configured to pass photoluminescence emitted by the electron spin defects while blocking another wavelength. For example, the electron spin defects may be excited by input light of a first wavelength, the photoluminescence may be substantially of a second wavelength, and the optical filter 420 may be configured to pass the second wavelength and block the first wavelength. Blocking the input light may be desirable, because otherwise some of the input light may be collected and contribute to measured photoluminescence magnitude, even though the input light is not photoluminescence. This can reduce a sensitivity of magnetic field collection (e.g., by introducing noise), or may lead to incorrect sensing determinations.

Various types of filters may be included. For example, the optical filter 420 may be a bandpass filter where the second wavelength is in the passband and the first wavelength is outside the passband, or the optical filter 420 may be a high-pass filter where the second wavelength is greater than the cutoff wavelength and the first wavelength is less than the cutoff wavelength. In some implementations, the optical filter 420 is a notch filter configured to block light of the first wavelength and pass light of other wavelengths above and below the first wavelength. In some implementations, multiple filters are included in each pixel magnetometer pixel 400.

In some implementations, each magnetometer pixel 400 does not include a corresponding optical filter; rather, filtering is performed at one or more photodetectors external to the magnetometer pixels.

Filtering operations such as "blocking" and "passing" are relative terms. For example, an output-coupled optical filter as described herein may "block" light of the first wavelength and "pass" light of the second wavelength in that the filter transmits a higher proportion of light of the second wavelength than light of the first wavelength.

The example magnetometer pixel 400 also includes a photodetector 422. The photodetector 422 is arranged to detect the photoluminescence emitted by the spin defects of the electron spin defect body 402. The photodetector 422 is arranged such that the photodetector 422 collects photoluminescence only from the electron spin defect body 402 and not from other electron spin defect bodies of other magnetometer pixels, or such that the photodetector 422 is much more sensitive to the photoluminescence from the electron spin defect body 402 than to electron spin defect bodies of the other magnetometer pixels. In some implementations, the reflector 410 and/or other light-blockers may contribute to this preferentially-local detection, e.g., by blocking photoluminescence from other magnetometer pixels.

In some implementations, the magnetometer pixel 400 includes an optical lens configured to focus light onto the photodetector 422. For example, the element 420 may include a lens instead of or in addition to a filter.

As described herein, the detected photoluminescence (e.g., a magnitude of the photoluminescence) is indicative of a magnetic field (e.g., a time-varying magnetic field) to which the electron spin defect body 402 is exposed.

In some implementations of an array of magnetometer pixels, each magnetometer pixel 400 does not include a corresponding photodetector 422; rather, one or more photodetectors each collect photoluminescence from a plurality of magnetometer pixels. For example, optical elements (e.g., lenses and/or mirrors) may be arranged to direct the photoluminescence from the plurality of magnetometer pixels to the corresponding one or more photodetectors.

Figure 12:
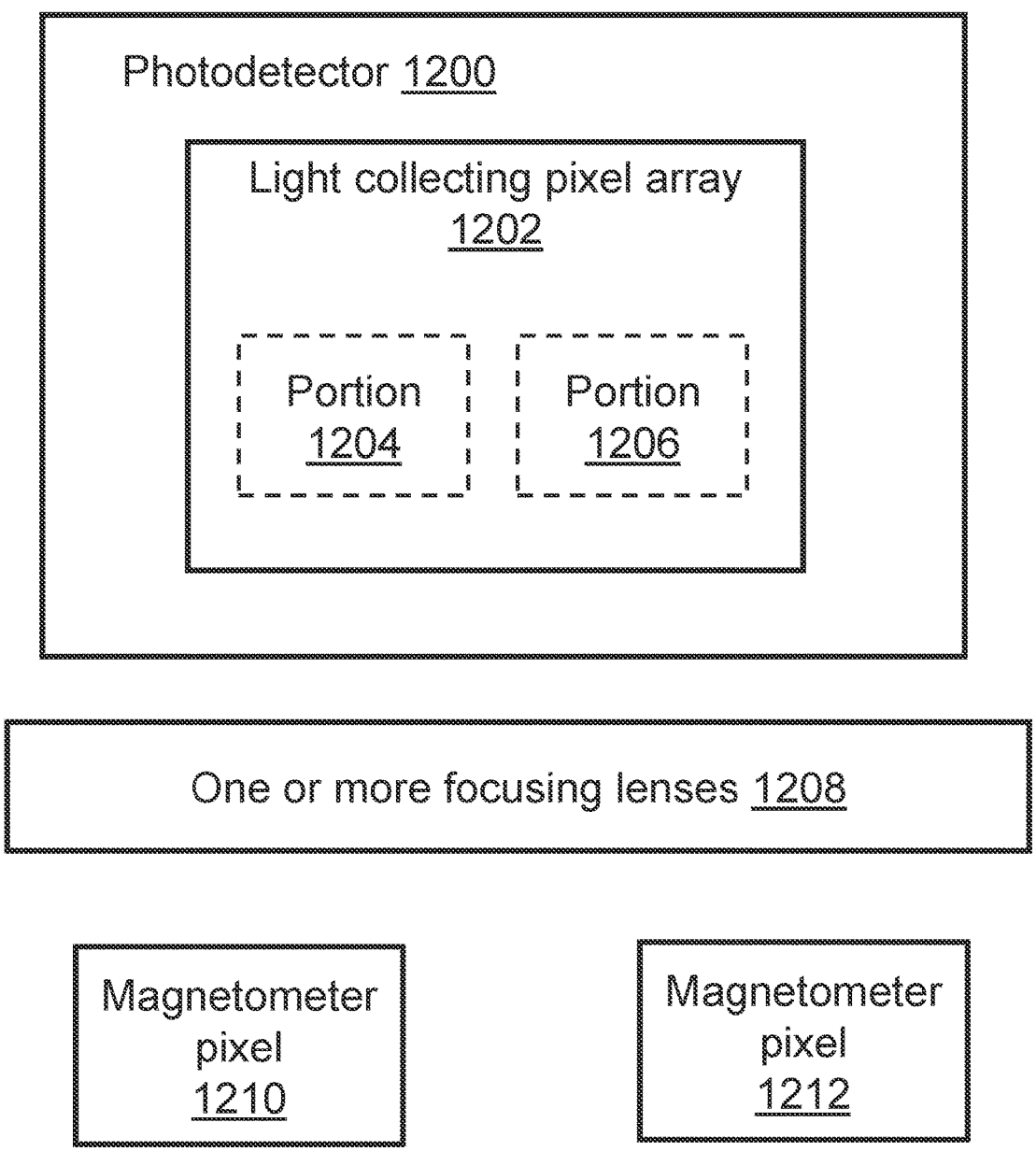
FIG. 12 is a schematic that illustrates an exemplary magnetometry device.

In such implementations, photoluminescence from different magnetometer pixels may be differentiated based on differentiated sensing by portions of each photodetector. For example, as shown in FIG. 12, each photodetector 1200 may include a light collecting pixel array 1202 (e.g., a CCD array), with respective portions 1204, 1206 of the light collecting pixel array being arranged to collect photoluminescence from different corresponding magnetometer pixels 1208. Identification of the particular portion detecting photoluminescence indicates the magnetometer pixel from which the photoluminescence was collected.

In some implementations, differentiated sensing is aided by one or more focusing lenses 1208 (e.g., arranged as shown for element 420) that focus photoluminescence onto spatially distinct segments of the light collecting pixel array 1202.

In some implementations in which one or more photodetectors each collect photoluminescence from a plurality of magnetometer pixels, photoluminescence from different magnetometer pixels may be differentiated based on time-gating. For example, an optical switch optically coupled to each magnetometer pixel may switch between which magnetometer pixel the photodetector collects from. Identification of the time of photoluminescence collection (and, for example, identification of a configuration of the optical switch at that time) indicates the magnetometer pixel from which the photoluminescence was collected. In some implementations, an optical switch switches which electron spin defect body is illuminated and thus generates photoluminescence, and time-gating may be performed based on this switching.

Optical switches (for either or both of switching which electron spin defect body is illuminated or switching which magnetometer pixel's photoluminescence is measured) may be integrated into or onto the substrate 404, e.g., as integrated circuits. In some implementations, the optical switch includes an on-chip acousto-optical modulator.

The example magnetometer 400 also includes a magnet 424. The magnet 424 may be arranged adjacent to the electron spin defect body 402. The magnet 424 is provided to induce the Zeeman effect and lift the degeneracy of the $m_s=+/-1$ spin sublevels. In some implementations, the magnet 424 is a permanent magnet. In some implementations, the magnet 424 is an electromagnet. The magnet 424 may be positioned directly on the substrate 404, on the electron spin defect body 402, and/or in another location. The magnet geometry may be chosen to minimize effects of inhomogeneous broadening between distinct defects in the electron spin defect body 402.

In some implementations (e.g., some scalar magnetometry implementations), the magnet 424 is arranged such that the bias magnetic field generated by the magnet 428 aligns with spin axes of the NV defects, e.g., projects equally onto multiple axes of the four possible orientation axes of the NV defects. For example, in a sample in which spin axes point along 0°-180° and 90°-270°, the magnet 424 might be arranged to apply a magnetic field in the 45°-225° direction, such that applied magnetic field strengths along the spin axes are equal and time-varying magnetic field strength along both axes is measured together.

In some implementations (e.g., some multi-vector magnetometry implementations), the magnet 424 is arranged so as to split PL intensity lines from the NV defects into four individual lines, representing the four possible orientation axes, by causing each spin axis to be exposed to a different magnetic field. For example, in the example given above, the magnet 424 (in some implementations, more than one magnet) would be arranged to apply different magnetic field strengths in the 0°-180° direction and the 90°-270°, such that time-varying magnetic field strengths along the axes may be measured independently.

Note that some implementations of arrays of magnetometer pixels do not include a magnet 424. Moreover, in some implementations, one or more magnets are included, but each of the one or more magnets is configured to apply a magnetic field to a plurality of magnetometer pixels.

Figure 6:
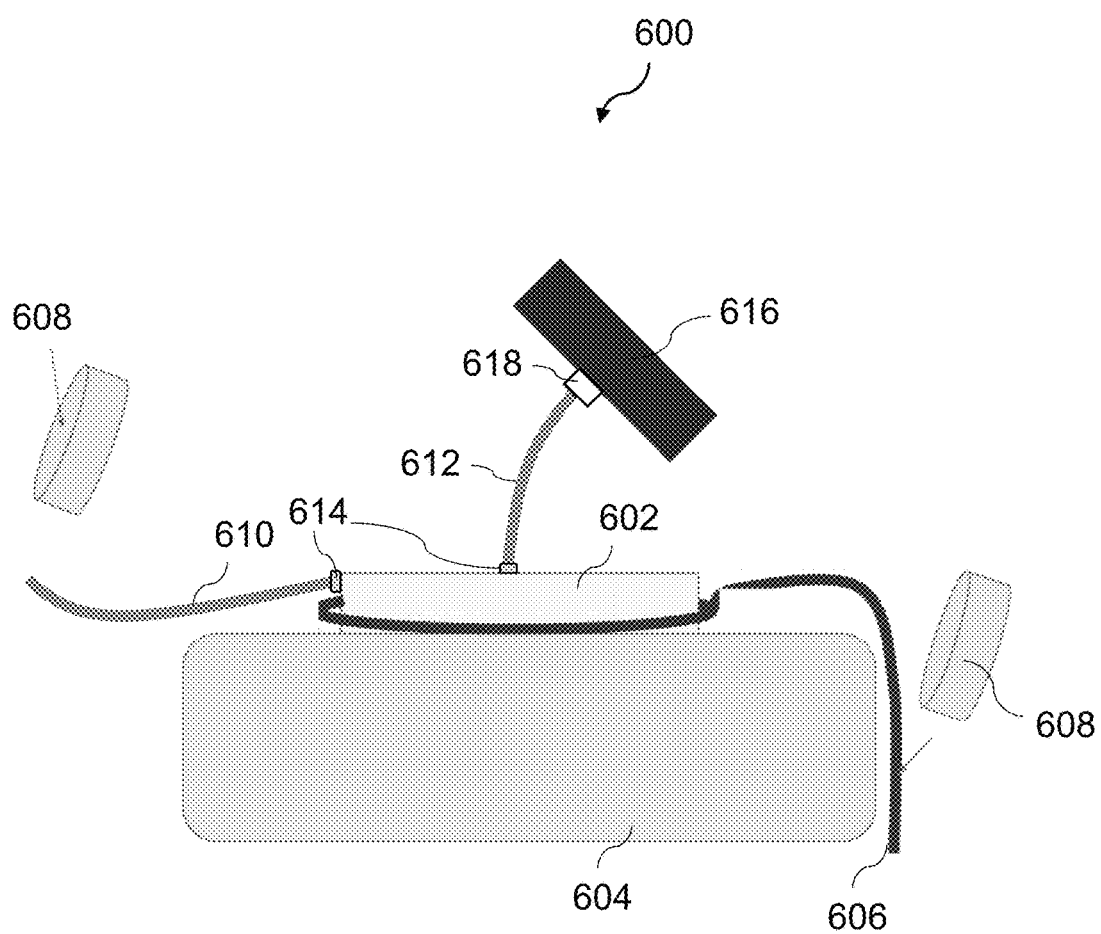
FIG. 6 is a schematic that illustrates an exemplary magnetometer pixel.

FIG. 6 is a schematic that shows another example of a magnetometer pixel 600. This magnetometer pixel 600 includes an electron spin defect body 602, a substrate 604, a microwave field transmitter 606, and a magnet 608. Except where indicated otherwise, the elements of magnetometer pixel 600 may be identical to those described for magnetometer pixel 400 and perform identical functions to those described for magnetometer pixel 400. In some implementations, the magnet 608 is not included.

An input optical fiber 610 and an output optical fiber 612 are attached to the electron spin defect body 602 and are arranged to, respectively, transmit input light into the electron spin defect body 602 and couple emitted photoluminescence out of the electron spin defect body 602. For example, ends of the optical fibers 610, 612 may be arranged to face surfaces of the electron spin defect body 500 to which the optical fibers 610, 612 are attached.

The terms "input" and "output" in reference to the optical fibers are merely labels referring to the arrangements of the optical fibers, without implying any necessary physical difference between the optical fibers. However, in some implementations the optical fibers are different, e.g., the input optical fiber may be configured to transmit light of the first wavelength and the output optical fiber may be configured to transmit light of the second wavelength.

The input light excites electron spin defects in the electron spin defect body 602. The electron spin defects then emit photoluminescence, at least some of which is collected by the output optical fiber. The input light may be generated by an optical source, as described in more detail below.

The optical fibers 610, 612 may be attached to the electron spin defect body 602 by an adhesive 614, which may be a different adhesive from an adhesive that attaches the electron spin defect body 602 to the substrate 604. Because, in some implementations, input light and/or photoluminescence pass through the adhesive 614, the adhesive 614 is configured to be substantially transparent to the input light and/or photoluminescence.

In some implementations, more than one input optical fiber 610 and/or more than one output optical fiber 612 are attached to the electron spin defect body 602. The use of multiple input optical fibers can increase a magnitude of excitation of the electron spin defects in the electron spin defect body 602, because light from each input optical fiber can excite spin defects in a respective portion of the electron spin defect body.

The use of multiple output optical fibers for photoluminescence can increase the efficiency of photoluminescence collection, because the output photoluminescence can be collected across a larger solid angle of emission from the electron spin defect body 602. In an equivalent free-space device, much of this photoluminescence might not be collected by collection lenses and/or photodetectors.

Compared to some magnetometer designs that include only free-space light transmission, the use of optical fibers can increase both excitation efficiency and photoluminescence collection efficiency. For example, reflection at the defect body/air interface may reduce a proportion of input light that is transmitted into the electron spin defect body 602 and/or photoluminescence that is transmitted out of the electron spin defect body 602. In addition, free-space scattering may also cause optical inefficiencies. Moreover, because emitted photoluminescence may be substantially contained in the output optical fibers, the photoluminescence is less likely to leak from one magnetometer pixel to another, potentially introducing error into measurements.

In some implementations, a quantum efficiency of photoluminescence detection, using optical fibers, is increased from about 4% to about 90% or higher, compared to a magnetometer with only free-space optical coupling. In various implementations, the quantum efficiency is between about 10% and 99%, between about 20% and 99%, or between about 50% and 99%.

The example magnetometer pixel 600 also includes a photodetector 616 optically coupled to the output optical fiber 612. Photoluminescence emitted from the electron spin defect body 602 is transmitted through the output optical fiber 612 and collected by the photodetector 616. As described above, this photoluminescence (e.g., a magnitude of the photoluminescence) is indicative of a magnetic field (e.g., a time-varying magnetic field) to which the electron spin defect body 602 is exposed.

As described for the example magnetometer pixel 400, there need not be a one-to-one relationship between the magnetometer pixel 600 and a corresponding photodetector. Rather, some implementations of an array of magnetometer pixels may include a photodetector that is optically coupled to output optical fibers from multiple magnetometer pixels/electron spin defect bodies. In such implementations, photoluminescence from different magnetometer pixels may be differentiated based on differentiated sensing by portions of the photodetector.

Additionally, or alternatively, the photoluminescence from different magnetometer pixels may be differentiated based on time-gating. For example, in some implementations, an optical switch is optically coupled to the output optical fibers and situated optically between the photodetector and the multiple magnetometer pixels in a multiplexed N×1 configuration. The optical switch is configured to switch which magnetometer pixel the photodetector collects from. In various implementations, the optical switch may be integrated into or onto the substrate 604, e.g., as an integrated circuit, or may be a separate unit.

In some implementations, an optical switch is coupled to the input optical fibers and situated optically between the optical source and the multiple magnetometer pixels in a multiplexed 1×N configuration. The optical switch is configured to switch which magnetometer pixel is illuminated by input light, such that collected photoluminescence may be assumed to be emitted by the illuminated magnetometer pixel.

In either case, identification of the time of photoluminescence collection (and a configuration of the optical switch at that time) indicates the magnetometer pixel from which the photoluminescence was collected.

In some implementations, the magnetometer pixel 600 includes an optical filter that performs an optical filtering function as described above for the optical filter 420. The optical filter in the magnetometer pixel 600 may be, for example, a fiber-embedded optical filter inside the output optical fiber 612 or a discrete fiber-coupled optical filter (e.g., a discrete fiber-coupled optical filter between the output optical fiber 612 and the photodetector 616, as shown in FIG. 6 as element 618). Other filter implementations (e.g., thin-film filters) are also possible.

Although example magnetometer pixels 400 and 600 have been shown separately, in some implementations an array of magnetometer pixels may include magnetometer pixels of both configurations. Moreover, in some implementations a magnetometer pixel may incorporate elements from both magnetometer pixels 400, 600. For example, input light may be provided to an electron spin defect body by an input optical fiber, and photoluminescence may be collected from the electron spin defect body using a reflector and free-space optics. As another example, input light may be provided using free-space optics and air-to-defect-body optical coupling, and photoluminescence may be collected using one or more output optical fibers.

Moreover, implementations according to this disclosure are not limited to the use of optical fibers and/or reflectors. In some implementations, other magnetometer configurations are used to ensure a sufficiently high amount of excited defect states and collected photoluminescence. For example, the use of high numerical aperture lenses and/or objectives, for either or both of excitation and collection, may result in sufficient photoluminescence detection.

Figure 7:
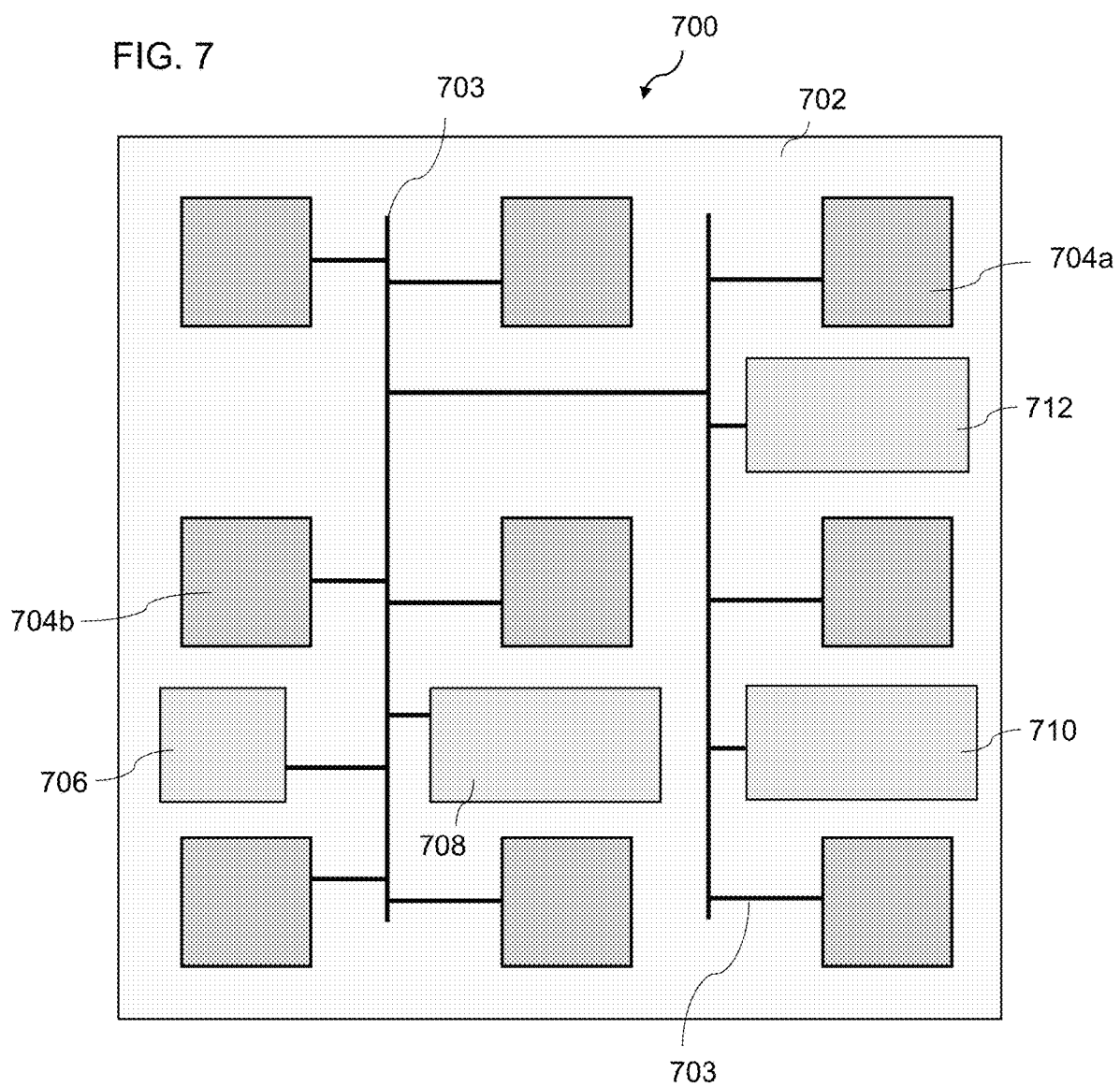
FIG. 7 is a schematic that illustrates an exemplary magnetometry device.

FIG. 7 is a schematic that shows an example magnetometry device 700. The device 700 includes a substrate 702 on which an array of magnetometer pixels (e.g., magnetometer pixels 704a, 704b) are disposed.

In some implementations, the magnetometer pixels are arranged in an array, e.g., a regular arrangement of equally-spaced rows and columns. In some implementations, the array includes at least three rows and at least three columns. In some implementations, the magnetometer pixels of the array lie in a single plane extending across the substrate 604.

In some implementations, each magnetometer pixel has lateral dimensions (e.g., width and/or length) between about 2 mm and about 10 mm. In some implementations, each magnetometer pixel has lateral dimensions less than about 10 mm. In some implementations, a total size of the array is about 10×10 cm. In various implementations, the array may include between 3 and 300 pixels.

The substrate 702 may be a semiconductor substrate (e.g., silicon), a dielectric substrate, or a printed circuit board (PCB). In some implementations, the electron spin defect bodies of the magnetometer pixels are disposed/attached directly on the substrate 702; in some implementations, the electron spin defect bodies are disposed on/attached to respective first substrates that are themselves disposed on/attached to the substrate 702. The attachments may be configured using adhesives, bonding, or another method.

In some implementations, optical, control, and/or sensing elements may be disposed on and/or integrated into the substrate 702. These elements may be coupled to one another and to the magnetometer pixels by on-chip optical and/or electrical coupling elements 703, e.g., metal PCB traces. The coupling elements 703 may be formed on a surface of the substrate 702, be buried inside the substrate 702, or both. Coupling elements 703 may also be separate from the substrate 604, e.g., wires, cables, and optical fibers.

The coupling elements 703 may be electrically and/or optically coupled to the magnetometer pixels, such that electrical and optical signals may be provided to and from the magnetometer pixels. For example, the coupling elements 703 may be bonded to the magnetometer pixels or connected to the magnetometer pixels via mesa connectors. These couplings may be to specific elements of the magnetometer pixels, e.g., to the microwave field transmitters and photodetectors of the magnetometer pixels. Accordingly, the coupling elements 703 may include both power lines and control lines connected to different inputs of each magnetometer pixel.

The device 700 may include a microwave field control circuit 706. The microwave field control circuit 706 may be formed in or on the substrate 702, for example, as an integrated circuit formed in the substrate itself or as an integrated circuit bonded to the substrate 702. For example, when the substrate 702 is a PCB, the microwave field control circuit 706 may be a circuit component electrically coupled to printed circuit elements of the PCB by wire bonding, ball bonding, or another coupling method. In some implementations, the microwave field control circuit 706 is a device that is separate from the substrate 702.

The microwave field control circuit 706 may be coupled, e.g., electrically connected, to the microwave field transmitters of one or more of the magnetometer pixels by the coupling elements 703. In some implementations, each magnetometer pixel corresponds to a respective microwave field control circuit 706. The microwave field control circuit 706 is configured to provide a microwave source signal to the microwave field transmitters so that the microwave field transmitters emits microwave fields toward the respective electron spin defect bodies of their magnetometer pixel. The microwave source signal may optionally be a pulsed microwave source signal.

In some implementations, a microwave frequency of the microwave source signal is between about 2 GHz and about 4 GHz. In some implementations, the microwave field transmitters (powered and/or controlled by the microwave field control circuit 706) each emit signals at multiple frequencies spaced apart from one another to drive additional energy level splittings. For example, in some implementations, a microwave field transmitter may be operated to emit microwave signals that address NV hyperfine transitions. In some implementations, the microwave field control circuit 706 is configured to provide a control signal that generates a pulsed microwave signal at the microwave field transmitters. In some implementations, the microwave field control circuit 706 is configured to provide a control signal that generates a continuous wave microwave signal at the microwave field transmitters.

The device 700 may also include an optical source 708 that is configured to emit input light to one or more of the magnetometer pixels. The input light emitted by the optical source 708 may include a first wavelength that excites the one or more lattice point defects within the electron spin defect bodies from a ground state to an excited state. The first wavelength is different from a second wavelength that is emitted by the lattice point defects upon relaxation. The first wavelength may be, e.g., about 532 nm to excite NV defects in the electron spin defect bodies. The optical source 708 may include, e.g., a light emitting diode, a laser, or a broadband source that includes filters configured to block transmission of wavelengths other than those of the first wavelength used to excite the lattice point defects.

A configuration of the optical source 708 depends on the configurations of the magnetometer pixels. If input light is provided to each electron spin defect body of each magnetometer pixel, the optical source 708 may emit the input light into one or more input optical fibers that are attached to one or more respective electron spin defect bodies. If input light is provided to each electron spin defect body by free-space transmission through a hole in a corresponding reflector, then the optical source 708 may emit the input light into free space, e.g., towards a collimating lens, an optical splitter (e.g., to split the input light into multiple beams to be directed to different respective electron spin defect bodies), a discrete optical filter, or a combination thereof.

Regardless of configurations of the magnetometers pixels, the optical source 708 or other optical elements optically coupled to the optical source may be arranged such that the input light and/or output light is transmitted through on-chip optical coupling elements of the substrate 702, e.g., on-chip integrated waveguides, on-chip integrated optical filters, on-chip collimating optics, on-chip optical switches, or a combination thereof, represented in FIG. 7 as coupling elements 703. The optical source 708 may itself be an integrated optical element, e.g., an on-chip integrated semiconductor laser or semiconductor light emitting diode. The optical source 708 may be a device that is disposed on (e.g., attached to and/or electrically bonded to) the substrate 702, as described for the microwave field control circuit 706. In some implementations, the optical source 708 is a device that is separate from the substrate 702.

In some implementations, the device 700 includes an optical source circuit, e.g., a driver 710 for the optical source 708, with the driver 710 coupled to the optical source 708 to provide a control signal to drive the optical source 708. The driver 710 may be formed in or on the substrate 404 or may be device that is separate from the substrate. For example, the driver 710 may be an integrated circuit bonded to the substrate 702. The driver 710 may be coupled, e.g., electrically connected, to the optical source 708 by the coupling elements 703.

In some implementations, the device 700 includes a processor 712. The processor 712 is coupled to one or more of the photodetectors (e.g., a photodetector for each magnetometer pixel or a photodetector receiving photoluminescence from multiple magnetometer pixels) to receive respective light measurement signals from each of the photodetectors. The processor 712 is configured to analyze the light measurement signals to determine the characteristics of the magnetic field to which the electron spin defect bodies of the device 700 are exposed.

In some implementations, the processor 712 performs operations to correlate light measurement signals to the magnetometer pixels providing the light measurement signals, e.g., time-gating, as described in more detail above.

The processor 712 may be formed in or on the substrate 702 (e.g., as an integrated circuit formed in the substrate 702 or bonded to the substrate 702) or may be a device that is separate from the substrate 702. The processor 712 may be coupled, e.g., electrically connected, to the photodetectors by the coupling elements 703. In some implementations, the processor 712 is located remotely from the device 700. For example, in some implementations, the device 700 includes a transmitter/receiver to wirelessly receive control and analysis signals from the processor 712 and to wirelessly transmit feedback and measurement data to the processor 712.

In some implementations, the processor 712 is coupled to one or both of the microwave field control circuit 706 and the driver 710 to control operations of the microwave field control circuit 706 and/or the driver 710.

The processor 712 may be configured to normalize magnetic field responses of the magnetometer pixels to one another so that measured magnetic field strengths between magnetometer pixels can be reliably cross-referenced to one another. For example, the processor 712 may tune each of the magnetometer pixels by adjusting one or more of: microwave frequency or microwave amplitude of the microwaves applied by the microwave transmitter of the magnetometer pixel, or intensity or polarization of the input light. One or more of these parameters is adjusted to cause $\partial I_0/\partial B$ to be approximately equal for each magnetometer pixel. The normalizing may be carried out under exposure to an external magnetic field or at zero external magnetic field.

In some implementations, the device 700 includes a computing device including one or more processors configured to perform the functions described herein for processor 712. The device 700 may include a memory and/or storage (e.g., computer-readable media) configured to store magnetic field measurement results, computer-readable instructions implementing operations disclosed herein, and other data.

As noted above, in some implementations some elements (e.g., magnets, photodetectors, and/or optical switches) are not integrated into each magnetometer pixel; rather, these elements may be formed in or on the substrate 702, or be devices separate from the substrate 702, in order to perform their functions for multiple magnetometer pixels. For example, a photodetector may be disposed on the substrate 702 and be arranged to receive photoluminescence from multiple magnetometer pixels, e.g., sequentially, simultaneously, or both. As another example, a magnet may be disposed on the substrate 702 and be arranged to apply magnetic fields to multiple magnetometer pixels.

Because coupling elements 703 are integrated into the substrate 702 on which the magnetometer pixels are disposed, the device 700 may be more compact and/or provide higher resolution magnetic field sensing than other magnetometry devices.

In some implementations, the device 700 includes an enclosure inside which the substrate 702 and associated elements are disposed. The enclosure may be formed from a material that allows magnetic fields to pass freely to the magnetometer pixels within the device 700, such as plastic. In some implementations, to allow for efficient thermal management and transfer of excess heat, the enclosure is formed from a metal or other thermal conductor, e.g., copper. The enclosure may be configured (e.g., by attachment elements such as straps and/or clips) to attach to objects whose magnetic fields are to be measured. For example, the enclosure may include clips or adhesive elements for attachment to the clothes or bodies of people, in order to perform spatially-resolved magnetocardiography.

Figure 8:
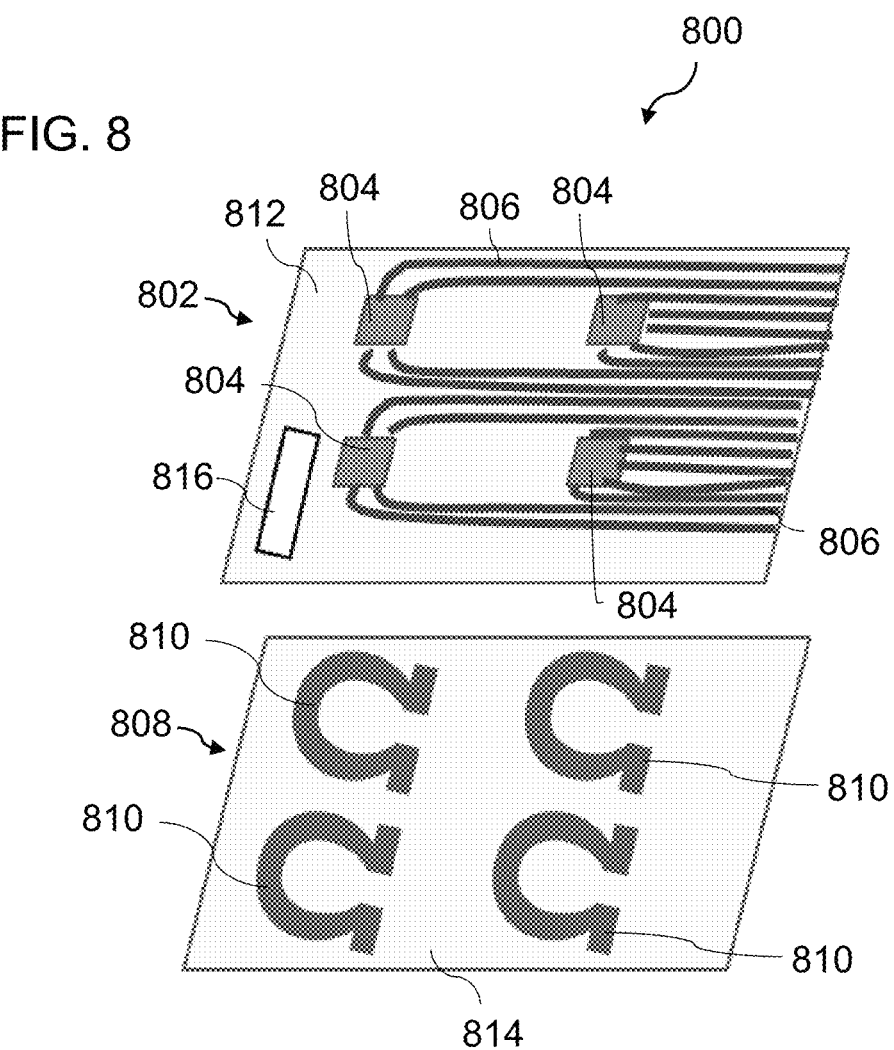
FIG. 8 is a schematic that illustrates an exemplary magnetometry device.

FIG. 8 shows a stacked-board design for an example magnetometry device 800. An array of electron spin defect bodies 804 is disposed on (e.g., attached to) a first circuit board 802. The electron spin defect bodies 804 are optically coupled to input and output optical fibers and/or on-chip waveguides (e.g., optical fibers and/or waveguides 806) that are optically coupled to one or more photodetectors and one or more optical sources (not shown), either separately or using one or more optical switches/multiplexers.

An array of microwave resonators 810 are disposed on or integrated into a second circuit board 808. The array of microwave resonators 810 is aligned with the array of electron spin defect bodies 804, such that, when the first circuit board 802 and second circuit board 808 are stacked on top of one another (e.g., by standoffs), each microwave resonator 810 is arranged to apply microwaves to a corresponding electron spin defect body 804 (e.g., is aligned with a corresponding electron spin defect body 804).

In some implementations, magnets are disposed on or integrated into the second circuit board 808 and arranged to apply magnetic fields to the electron spin defect bodies 804. In some implementations, magnets disposed on or integrated into the first circuit board 802.

In some implementations, the first circuit board 802 and second circuit board 808 are made from different materials. For example, the first circuit board 802 may be an optical circuit board that is at least partially transparent. In some implementations, the first circuit board 802 includes embedded glass to transmit light within the first circuit board 802.

The second circuit board 808 may be a printed circuit board, a silicon substrate, or another substrate. In some implementations, the second circuit board 808 includes (e.g., is substantially made of) a low-loss dielectric laminate that reduces microwave losses to efficiently transfer microwaves to the array of electron spin defect bodies 804.

In some implementations, the first circuit board 802 and second circuit board 808 are arranged in a flipped configuration such that the electron spin defect bodies 804 on a first surface 812 of the first circuit board 802 face microwave resonators 810 on a first surface 814 of the second circuit board 808. In some implementations, the surfaces 812, 814 do not face each other (e.g., are oriented in the same direction).

In some implementations, a heatsink 816 is attached to one or both boards 802, 808 to provide thermal stability to the electron spin defect bodies 804.

Other components disclosed in reference to FIG. 7 or in reference to other magnetometry devices of this disclosure may be disposed on either circuit board 802, 808. For example, either or both circuit boards 802, 808 may include integrated metal traces, control and drive circuits, etc. In some implementations, elements on the two circuit boards 802, 808 are coupled, e.g., by mezzanine connectors built into mating components that mount the circuit boards 802, 808 together.

Figure 9:
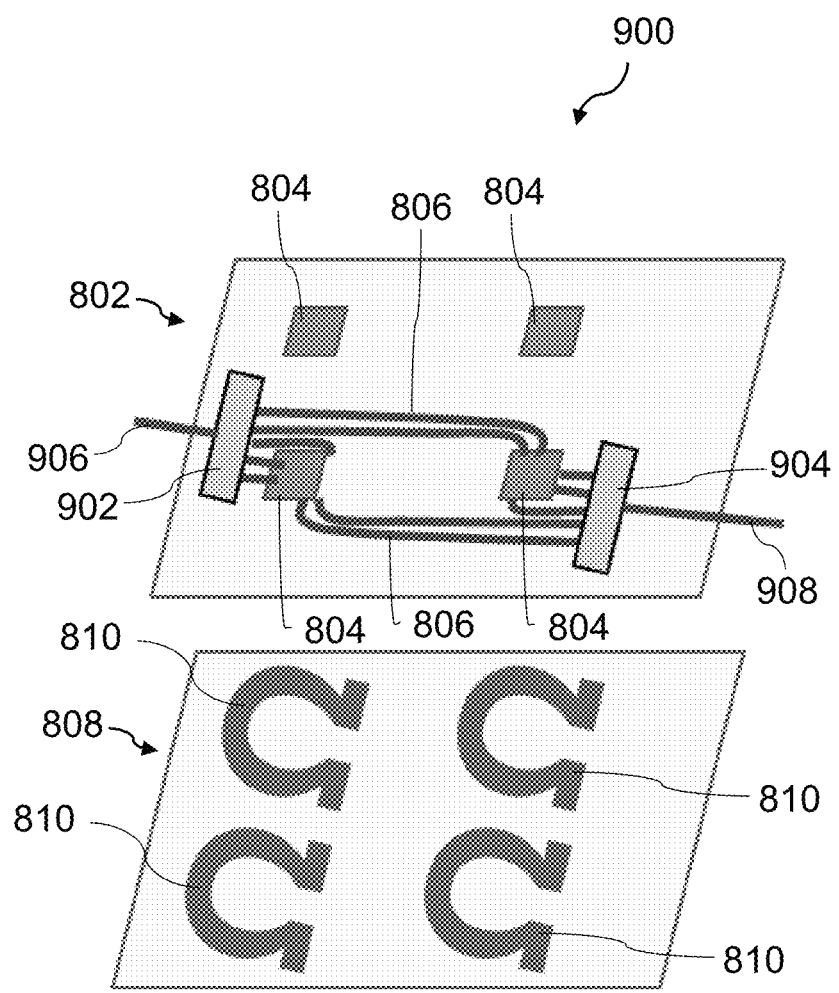
FIG. 9 is a schematic that illustrates an exemplary magnetometry device.

FIG. 9 shows another example of a magnetometry device 900 using a stacked-board design. Unless indicated otherwise, components of the magnetometry device 900 may be as described for the magnetometry device 800.

As described for the magnetometry device 800, a first circuit board 802 includes an array of electron spin defect bodies 804. A second circuit board 808 includes an array of microwave resonators 810 arranged to align with and transmit microwaves to the array of electron spin defect bodies 804 when the circuit boards 802, 808 are stacked.

Optical fibers and/or on-chip waveguides 806 optically couple the electron spin defect bodies 804 to an input optical multiplexer 902 and an output optical multiplexer 904, each of which may be integrated into the first circuit board 802 or mounted on the first circuit board 802, e.g., as discrete optical devices. The input optical multiplexer 902 and output optical multiplexer 904 are configured to implement optical switching such that a) photoluminescence is collected from one electron spin defect body 804 at a time, by switching of the output optical multiplexer 904, b) photoluminescence is excited in one electron spin defect body 804 at a time, by switching of the input optical multiplexer 902, or c) both, with the input optical multiplexer 902 and the output optical multiplexer 904 synchronized with one another. Additional optical fibers 906, 908 couple to an input optical source and a photodetector, respectively (not shown).

In some implementations, only one of the optical multiplexers 902, 904 implements switching, and control of only the input optical side or output optical side is sufficient to obtain distinct, distinguishable signals from the plurality of electron spin defect bodies 804.

Because the photoluminescence from each magnetometer pixel of the array of magnetometer pixels is indicative of the local magnetic field of the magnetometer pixel, signals representative of the photoluminescences may be analyzed to reconstruct a spatial map of an overall magnetic field to which the array of magnetometer pixels is exposed. That is, an array of magnetometer pixels, with appropriate supporting electronics, can function as a magnetic field imager analogous to an array of photosensitive pixels usable for conventional imaging.

Figure 10:
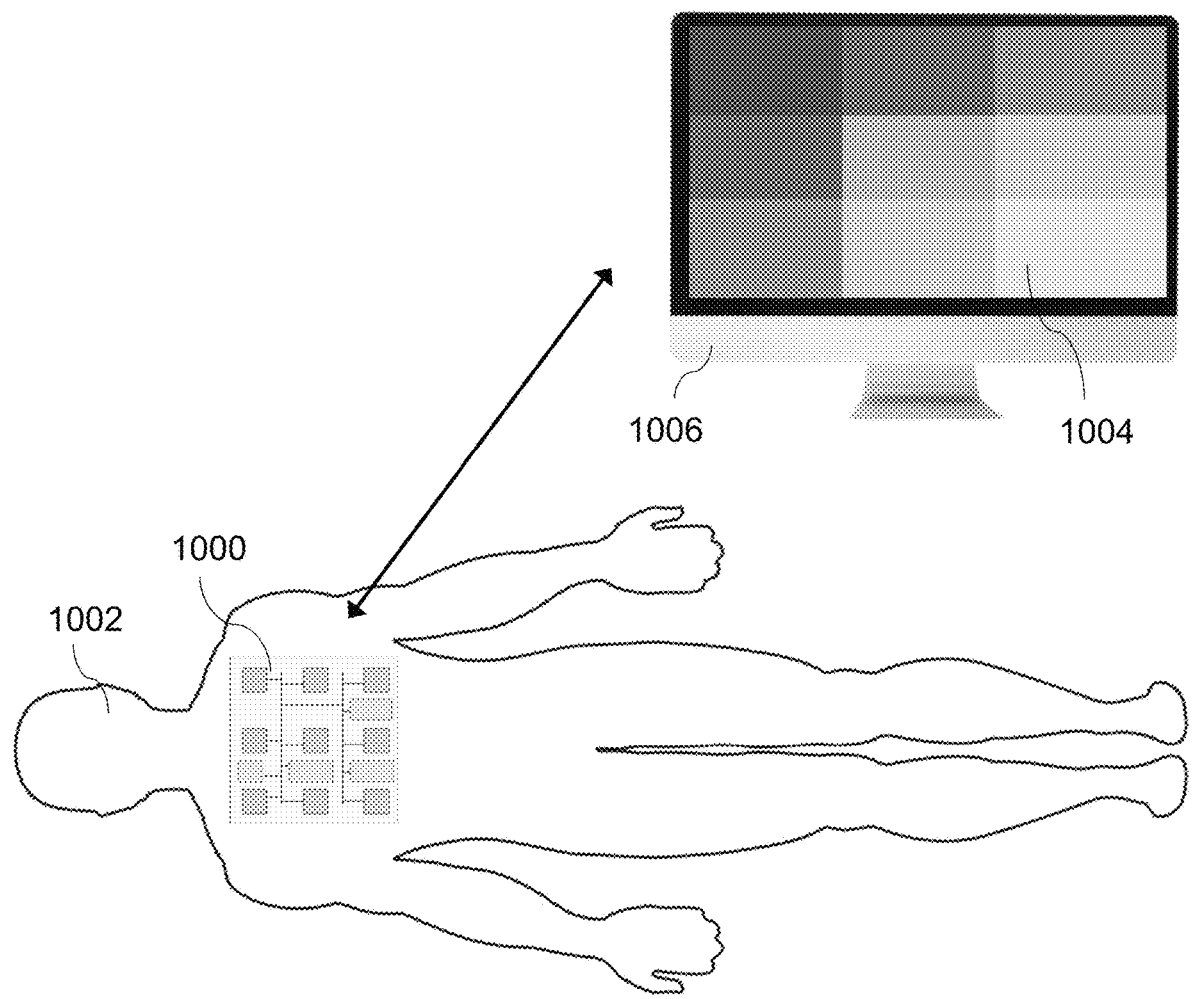
FIG. 10 is a schematic that illustrates an example application of a magnetometry device.

For example, as shown in FIG. 10, a magnetometry device 1000 (e.g., device 700) is attached to a chest of a person 1002. A processor of the magnetometry device 1000 (e.g., processor 712) or another processor receives light measurement signals from the one or more photodetectors of the device 1000, the light measurement signals indicative of photoluminescence emitted by the electron spin defect bodies of the magnetometer pixels of the device 1000. Based on these light measurement signals and based on positions of each of the magnetometer pixels, the processor determines magnetic field characteristics of each of those positions, e.g., the processor may determine magnetic field strength and/or magnetic field orientation at each of those positions.

In some implementations, the processor is configured to reconstruct a maximum-likelihood estimate for the magnetic field in three spatial dimensions and as a function of time. Inputs on which the maximum-likelihood estimate can be based may include one or more of: measured photoluminescence from multiple magnetometer pixels, system calibration information, known noise sources, an expected source of the magnetic field, or other data. Based on the maximum-likelihood estimate, the overall magnetic field is determined.

The spatially-resolved determinations about the magnetic field may be combined into an image, e.g., a heatmap 1004 of magnetic field strength displayed on a monitor 1006. The monitor 1006 may be, for example, a monitor of a computer, a mobile computing device, or a dedicated display. In some implementations, a wireless networking unit of the device 1000 is configured to transmit the magnetic field data wirelessly, e.g., over the Internet, over a local wireless connection, or both.

In this example, the heatmap 1004 represents a magnetic field image of a heart of the person 1002.

Figure 11:
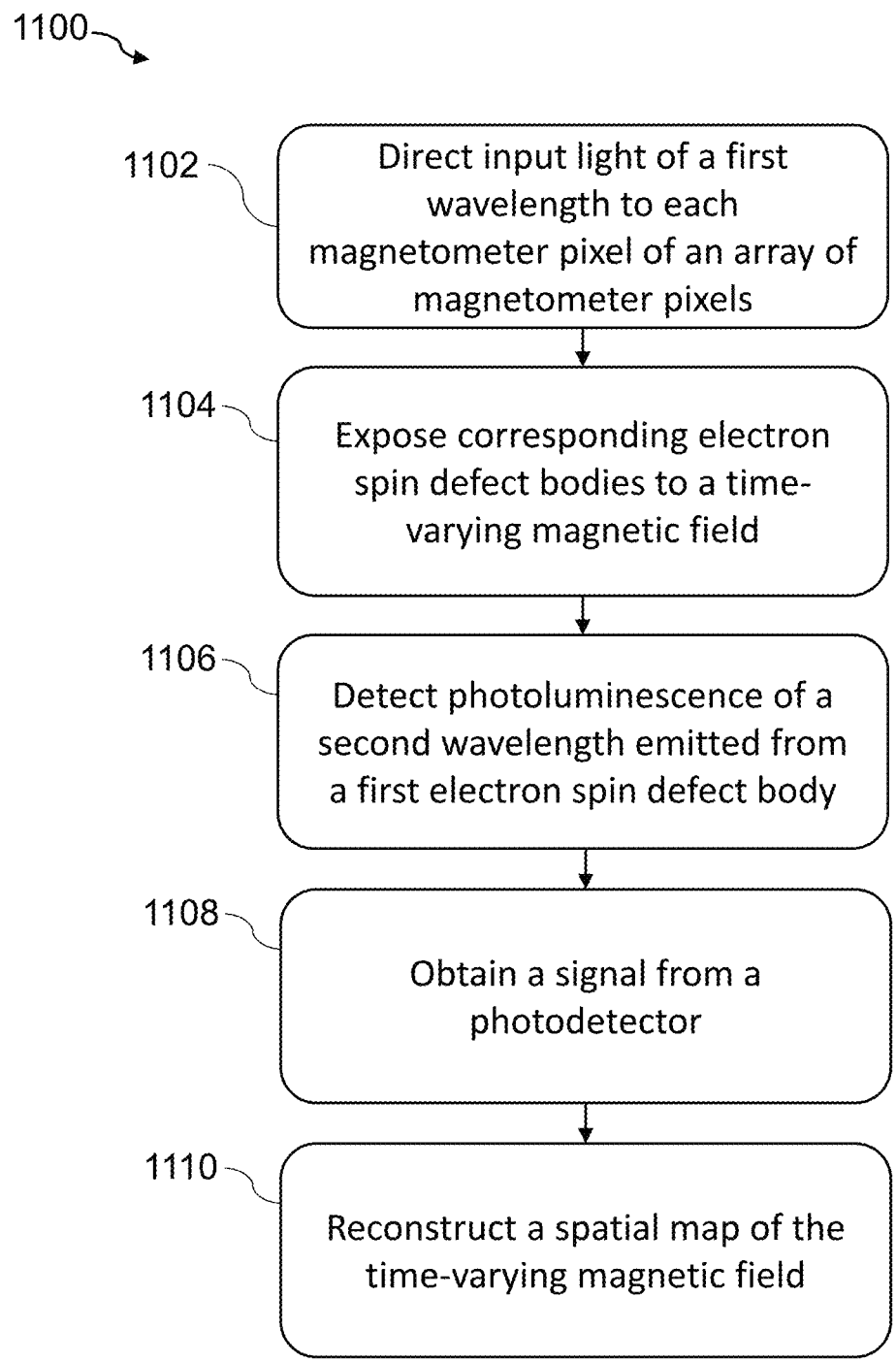
FIG. 11 is a flowchart that illustrates an exemplary magnetometry method.

FIG. 11 shows an example method 1100 according to some implementations of this disclosure. Input light of a first wavelength is directed to each magnetometer pixel of an array of magnetometer pixels (1102). Corresponding electron spin defect bodies are exposed to a time-varying magnetic field (1104). Photoluminescence of a second wavelength is detected emitted from a first electron spin defect body (1106). A signal is obtained from a photodetector (1108). A spatial map of the time-varying magnetic field is reconstructed (1110). Other details and possible additional features of the example method 1100 are described throughout this disclosure.

The electron spin defect based magnetometry techniques and devices described herein are viable for compact, room temperature magnetometry, and are robust to large magnetic field variations. In some implementations, the magnetometer can be used in applications such as magnetocardiography to detect magnetic fields from the heart. In particular, compact, robust spin defect based magnetometers may be used to detect magnetic fields emanating from the heart for continuous, long-term monitoring and early detection of various cardiac conditions.

Cardiovascular disease is the number one cause of death worldwide. Electric and magnetic fields generated by the heart contain information about the onset of a dangerous condition such as a heart attack or arrhythmia. However, technologies for monitoring this vital organ may be bulky, noisy, and in non-clinical settings can only be used for up to a few days at a time, making the continuous acquisition of data over at best problematic. Moreover, current analyses must be performed by a medical professional after the data is taken, severely limiting the amount of data that can be analyzed and further increasing the cost (and decreasing the scope and accessibility) of these vital services.

The sensors required to detect the small magnetic fields tend to require operation in a shielded room (such as optically pumped magnetometers), or at cold temperatures (such as SQUIDS), making continuous acquisition and monitoring difficult. The magnetometers disclosed herein may be used, in certain implementations, as quantum sensors to measure magnetic fields from the heart and may be operated outside of a shielded room, at room temperature and offer a large dynamic range of up to 100 mT. Moreover, the device may be constructed so it is compact and can be worn comfortably and close to the body.

The magnetometers described herein may also be used in applications besides magnetocardiography. For example, the magnetometers may be used to measure neuron activity. In some cases, the magnetometers may be used to detect magnetic fields created by electrical currents on a chip, thereby directly mapping on-chip circuit activity. The magnetometers described in this disclosure may be used in any application in which high-sensitive magnetic field measurement is desired.

Embodiments and functional operations described in this specification, such as the operations and analysis performed by the processor, the microwave control circuit, and the optical source driver, may be implemented in digital electronic circuitry, or in computer software, firmware, or hardware, including the structures disclosed in this specification and their structural equivalents, or in combinations of one or more of them. Embodiments (e.g., operations described as being performed by a processor, a switch, a microwave control circuit, an optical source driver, or other components) may be implemented as one or more computer program products, i.e., one or more modules of non-transient computer program instructions encoded on a non-transient computer readable medium for execution by, or to control the operation of, a data processing apparatus. The computer readable medium may be a machine-readable storage device, a machine-readable storage substrate, a memory device, a composition of matter effecting a machine-readable propagated signal, or a combination of one or more of them.

The term "data processing apparatus" encompasses all apparatus, devices, and machines for processing data, including by way of example a programmable processor, a computer, or multiple processors or computers. The apparatus may include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal that is generated to encode information for transmission to suitable receiver apparatus.

A computer program (also known as a program, software, software application, script, or code) may be written in any form of programming language, including compiled or interpreted languages, and it may be deployed in any form, including as a stand-alone program or as a module, component, subroutine, or other unit suitable for use in a computing environment. A computer program does not necessarily correspond to a file in a file system. A program may be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program may be deployed to be executed on one computer or on multiple computers that are located at one site or distributed across multiple sites and interconnected by a communication network.

Processors suitable for the execution of a computer program include, by way of example, both general and special purpose microprocessors, and any one or more processors of any kind of digital computer. Generally, a processor will receive instructions and data from a read only memory or a random access memory or both.

While this specification contains many specifics, these should not be construed as limitations on the scope of the disclosure or of what may be claimed, but rather as descriptions of features specific to particular embodiments. Certain features that are described in this specification in the context of separate embodiments may also be implemented in combination in a single embodiment. Conversely, various features that are described in the context of a single embodiment may also be implemented in multiple embodiments separately or in any suitable subcombination. Moreover, although features may be described above as acting in certain combinations and even initially claimed as such, one or more features from a claimed combination may in some cases be excised from the combination, and the claimed combination may be directed to a subcombination or variation of a subcombination.

Similarly, while operations are described as being performed in a particular order, this should not be understood as requiring that such operations be performed in the particular order disclosed, or that all disclosed operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems may generally be integrated together in a single software product or packaged into multiple software products A number of embodiments have been described. Nevertheless, it will be understood that various modifications may be made without departing from the spirit and scope of the invention. Accordingly, other embodiments are within the scope of the following claims.

What is claimed is:

1. A magnetometry apparatus comprising:
    an array of magnetometer pixels, each magnetometer pixel of the array of magnetometer pixels comprising:
        a respective electron spin defect body comprising a plurality of lattice point defects, and
        a respective microwave field transmitter configured to apply a microwave field to the electron spin defect body of the magnetometer pixel;
    an optical source configured to emit input light of a first wavelength that excites the plurality of lattice point defects of the electron spin defect bodies of the magnetometer pixels of the array of magnetometer pixels from a ground state to an excited state; and
    a photodetector arranged to receive photoluminescence of a second wavelength emitted from a plurality of the electron spin defect bodies of the magnetometer pixels of the array of magnetometer pixels,
    wherein the photodetector comprises a light collecting pixel array, and wherein the photodetector and the plurality of electron spin defect bodies are arranged such that respective photoluminescences emitted from the plurality of electron spin defect bodies are received at respective distinct portions of the light collecting pixel array, and
    wherein the second wavelength is different from the first wavelength.

2. The apparatus of claim 1, wherein each magnetometer pixel of the array of magnetometer pixels comprises a respective substrate on which the electron spin defect body of the magnetometer pixel is disposed.

3. The apparatus of claim 1, comprising a common substrate on which the electron spin defect bodies of the magnetometer pixels of the array of magnetometer pixels are disposed.

4. The apparatus of claim 3, wherein the common substrate comprises a metal trace that electrically couples the photodetector to a processor disposed on the common substrate.

5. The apparatus of claim 1, comprising a plurality of lenses arranged to focus the respective photoluminescences onto the respective distinct portions of the light collecting pixel array.

6. The apparatus of claim 1, comprising a computing device coupled to the photodetector, the computing device configured to perform operations comprising:
    receiving, from the photodetector, signals indicative of the respective photoluminescences emitted from the plurality of electron spin defect bodies, and
    reconstructing a spatial map of a second magnetic field to which the array of magnetometer pixels is exposed based, at least in part, on the signals indicative of the respective photoluminescences.

7. The apparatus of claim 6, wherein reconstructing the spatial map comprises generating an image representing the second magnetic field to which the array of magnetometer pixels is exposed.

8. The apparatus of claim 6, wherein the operations comprise normalizing respective magnetic field responses of each of the magnetometer pixels.

9. The apparatus of claim 1, wherein each magnetometer pixel comprises a respective parabolic reflector, and wherein each parabolic reflector defines an internal cavity in which the electron spin defect body of the magnetometer pixel is arranged.

10. The apparatus of claim 1, wherein each magnetometer pixel comprises a respective optical filter configured to pass light of the second wavelength and block light of the first wavelength.

11. The apparatus of claim 9, wherein each parabolic reflector comprises an opening through which the input light of the first wavelength passes.

12. The apparatus of claim 1, comprising:
    a first optical fiber arranged to carry the input light from the optical source to a first electron spin defect body of a first magnetometer pixel of the magnetometer pixels of the array of magnetometer pixels; and
    a second optical fiber arranged to carry the photoluminescence from the first electron spin defect body to the photodetector.

13. The apparatus of claim 12, wherein the first optical fiber and the second optical fiber are attached to the first electron spin defect body of the first magnetometer pixel.

14. The apparatus of claim 1, comprising at least one optical filter between the array of magnetometer pixels and the photodetector, wherein the at least one optical filter is configured to pass light of the second wavelength and block light of the first wavelength.

15. The apparatus of claim 1, comprising a magnet configured to apply a magnetic field to the array of magnetometer pixels.

16. The apparatus of claim 1, wherein the electron spin defect bodies of the magnetometer pixels of the array of magnetometer pixels are disposed on a first common substrate, and
    wherein the microwave field transmitters of the magnetometer pixels of the array of magnetometer pixels are disposed on a second substrate.

17. The apparatus of claim 16, wherein the first common substrate is mounted on the second substrate such that each electron spin defect body is aligned with a corresponding microwave field transmitter.

18. A method of spatially mapping a time-varying magnetic field, comprising:
- directing input light of a first wavelength to each magnetometer pixel of an array of magnetometer pixels, each magnetometer pixel of the array of magnetometer pixels comprising a respective electron spin defect body comprising a plurality of lattice point defects;
- exposing the respective electron spin defect body of each magnetometer pixel of the array of magnetometer pixels to the time-varying magnetic field;
- detecting, at a photodetector, respective photoluminescences of a second wavelength emitted from a plurality of the electron spin defect bodies of the magnetometer pixels of the array of magnetometer pixels, wherein the second wavelength is different from the first wavelength,
  - wherein the photodetector comprises a light collecting pixel array, and wherein detecting the respective photoluminescences comprises receiving the respective photoluminescences at respective distinct portions of the light collecting pixel array;
- obtaining a signal from the photodetector, wherein the signal is indicative of the photoluminescences; and
- reconstructing a spatial map of the time-varying magnetic field based, at least in part, on the signal.

19. The method of claim 18, wherein reconstructing the spatial map comprises generating an image representing spatially-resolved magnetic field strengths of the time-varying magnetic field.

20. The method of claim 18, comprising normalizing respective magnetic field responses of each of the magnetometer pixels.

21. The method of claim 18, wherein directing the input light comprises providing the input light into each optical fiber of a plurality of optical fibers, each optical fiber of the plurality of optical fibers having an end attached to a corresponding magnetometer pixel of the array of magnetometer pixels, wherein each optical fiber is arranged to direct the input light into the electron spin defect body of the corresponding magnetometer pixel.

22. The method of claim 18, wherein each magnetometer pixel comprises a respective parabolic reflector, wherein the parabolic reflector defines an internal cavity in which the electron spin defect body of the magnetometer pixel is arranged, and wherein directing the input light comprises directing the input light through respective openings in the parabolic reflectors.

23. The method of claim 18, comprising filtering the respective photoluminescences to block light of the first wavelength and pass light of the second wavelength.

24. The method of claim 18, comprising applying microwave signals to the electron spin defect bodies of the array of magnetometer pixels.

25. The method of claim 18, comprising applying a second magnetic field to the electron spin defect bodies of the array of magnetometer pixels.

26. A magnetometry apparatus comprising:
- an array of magnetometer pixels, each magnetometer pixel of the array of magnetometer pixels comprising:
  - a respective electron spin defect body comprising a plurality of lattice point defects, and
  - a respective microwave field transmitter configured to apply a microwave field to the electron spin defect body of the magnetometer pixel,
    - wherein the electron spin defect bodies of the magnetometer pixels of the array of magnetometer pixels are disposed on a first common substrate, and
    - wherein the microwave field transmitters of the magnetometer pixels of the array of magnetometer pixels are disposed on a second substrate;
- an optical source configured to emit input light of a first wavelength that excites the plurality of lattice point defects of the electron spin defect bodies of the magnetometer pixels of the array of magnetometer pixels from a ground state to an excited state; and
- a photodetector arranged to receive photoluminescence of a second wavelength emitted from a first electron spin defect body of a first magnetometer pixel of the array of magnetometer pixels,
- wherein the second wavelength is different from the first wavelength.

27. The magnetometry apparatus of claim 26, wherein the first common substrate and the second common substrate are arranged in a flipped configuration, such that the electron spin defect bodies of the magnetometer pixels of the array of magnetometer pixels, on a first surface of the first common substrate, face the microwave field transmitters of the magnetometer pixels of the array of magnetometer pixels, on a first surface of the second substrate.

28. The magnetometry apparatus of claim 26, wherein the first common substrate comprises embedded glass.

29. The magnetometry apparatus of claim 26, wherein the second substrate comprises a dielectric laminate.

30. The magnetometry apparatus of claim 26, wherein the first common substrate is mounted on the second substrate such that each electron spin defect body is aligned with a corresponding microwave field transmitter.

31. The magnetometry apparatus of claim 26, wherein the first common substrate comprises a plurality of on-chip waveguides for providing the input light to the electron spin defect bodies of the magnetometer pixels of the array of magnetometer pixels.

32. The magnetometry apparatus of claim 26, wherein the first common substrate is at least partially transparent.

* * * * *